(12) United States Patent
Coassin et al.

(10) Patent No.: US 6,517,781 B1
(45) Date of Patent: *Feb. 11, 2003

(54) LOW FLUORESCENCE ASSAY PLATFORMS AND RELATED METHODS FOR DRUG DISCOVERY

(75) Inventors: Peter J. Coassin, Encinitas, CA (US); Alec Tate Harootunian, Del Mar, CA (US); Andrew A. Pham, Del Mar, CA (US); Harry Stylli, San Diego, CA (US); Roger Y. Tsien, La Jolla, CA (US)

(73) Assignee: Aurora Biosciences Corporation, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/476,959

(22) Filed: Jan. 3, 2000

Related U.S. Application Data

(63) Continuation of application No. 09/030,578, filed on Feb. 24, 1998, now Pat. No. 6,171,780, which is a continuation-in-part of application No. 08/868,049, filed on Jun. 3, 1997, now Pat. No. 5,910,287, which is a continuation-in-part of application No. 08/867,584, filed on Jun. 2, 1997, which is a continuation-in-part of application No. 08/868,018, filed on Jun. 3, 1997, which is a continuation-in-part of application No. 08/867,567, filed on Jun. 2, 1997.

(51) Int. Cl.$^7$ .................................................. B01L 3/00
(52) U.S. Cl. ..................... 422/102; 422/99; 422/100; 435/283.1; 435/288.3; 435/288.4
(58) Field of Search ..................... 422/99, 100, 101, 422/102; 435/287, 293, 300, 808, 970, 283.1, 287.1, 288.1, 288.3, 288.4

(56) References Cited

U.S. PATENT DOCUMENTS

| | | | | |
|---|---|---|---|---|
| 5,487,872 A | * | 1/1996 | Hafeman et al. | 422/102 |
| 5,792,426 A | * | 8/1998 | Portmann et al. | 422/102 |
| 5,910,287 A | * | 6/1999 | Coassin et al. | 422/102 |
| 6,063,338 A | * | 6/2000 | Pham et al. | 422/61 |

* cited by examiner

*Primary Examiner*—Jill Warden
*Assistant Examiner*—Dwayne K Handy
(74) *Attorney, Agent, or Firm*—Gray, Cary, Ware & Friedenrich LLP; Lisa A. Haile

(57) ABSTRACT

One aspect of the present invention is a multi-well platform for fluorescence measurements, comprising a plurality of wells within a frame, wherein the multi-well platform has low fluorescence background. Another aspect of the present invention is a system for spectroscopic measurements, comprising reagents for an assay and a multi-well platform for fluorescence measurements. A further aspect of the present invention is a method for detecting the presence of an analyte in a sample contained in a multi-well platform by detecting light emitted from the sample. Another aspect of the present invention is a method from identifying a modulator of a biological process or target in a sample contained in a multi-well platform by detecting light emitted from the sample. Another aspect of the present invention is a composition identified by this method. A further aspect of the present invention is a method to identify a therapeutic. A further aspect of the present invention is a method of testing a therapeutic for therapeutic activity and toxicology by identifying a therapeutic using a method of the present invention and monitoring the toxicology and efficacy of the therapeutic in an in vivo model.

28 Claims, 4 Drawing Sheets

LOW FLUORESCENCE ASSAY PLATFORMS AND RELATED METHODS FOR DRUG DISCOVERY

This is a continuation of application Ser. No. 09/030,578, filed Feb. 24, 1998 now U.S. Pat. No. 6,171,780, which is a continuation-in-part of application Ser. No. 08/868,049, filed Jun. 3, 1997, now U.S. Pat. No. 5,910,287, which is a continuation-in-part of application Ser. No. 08/867,584, filed Jun. 2, 1997; and application Ser. No. 09/030,578 is also a continuation-in-part of application Ser. No. 08/868,018, filed Jun. 3, 1997, which is a continuation-in-part of application Ser. No. 08/867,567, filed Jun. 2, 1997 and is also related to application Ser. No. 09/028,283, filed Feb. 24, 1998. The benefit of priority of each of the above-referenced applications is expressly claimed and the disclosures of each are hereby incorporated by reference in their entirety.

TECHNICAL FIELD

The present invention generally relates to multi-well platforms for use in spectroscopic measurements and methods of using such multi-well platforms. Multi-well platforms are particularly useful for fluorescence measurements of chemical or biological samples. The multi-well platforms can be used in automated and integrated systems and methods for rapidly identifying chemicals with biological activity in liquid samples, particularly automated screening of low volume samples for new medicines, agrochemicals, or cosmetics.

BACKGROUND

A number of multi-well platforms are commercially available for culturing cells or performing chemical or cellular assays. While many of these multi-well platforms offer the desirable features of biocompatibility, ease of manufacture and substantial structural integrity, the inventors of the present invention have generally found that these multi-well platforms, especially plates with polymeric bottoms, suffer from a substantially high degree of fluorescence. The relatively high amount of background fluorescence inherent in commercially available multi-well platforms with polymeric bottoms makes such multi-well platforms generally not suitable for highly sensitive fluorescence measurements associated with many assays.

In the course of miniaturizing and automating screening assays, the inventors of the present invention realized that existing multi-well platforms were generally not suited for assay volumes of a microliter or less. The inventors of the present invention discovered that when existing multi-well platforms were used for such small volumes, the assay became unpredictable and sometimes inoperable. Others have used a variety of multi-well platforms in an attempt to produce a multi-well platform suitable for miniaturization, but none of these multi-well platforms were found by the present inventors to be suitable for their applications. Having discovered this previously unrecognized problem, the inventors of the present invention set out to make a multi-well platform compatible with miniaturized assays, such as fluorescent based assays.

The inventors prepared selection criteria for suitable materials for manufacturing multi-well platforms for such applications. As a key example of the selection criteria, which is more fully described herein, the inventors investigated the spectral properties of various materials, including their fluorescence and transmittance, for compatibility with spectroscopic measurements of chemical and biological events. Such materials would also desirably, but not necessarily depending on the application, have biocompatibility, relative chemical inertness, and sufficient rigidity for the application at hand, and ease of manufacture. The inventors selected a variety of materials for testing based, in part, on the structural features of the materials, which is more fully described herein. The inventors' search for materials included searching fields not associated with spectroscopic measurements, such as the electronics and audio recording arts. The inventors compared a variety of materials to glass that has relatively minor inherent fluorescence. The inventors realized that fused silica would tend to have less inherent fluorescence than glass.

As described herein the inventors for the first time have developed novel multi-well platforms that offer excellent performance characteristics in fluorescent assays. Such multi-well platforms can be used in conventional 96-well formats or higher density formats, such as less than 864 wells per platform or 864 or more wells per platform. Higher density formats, such as greater than 3,000 wells per multi-well platform, are also part of the invention.

Systems and methods for rapidly identifying chemicals with biological activity in samples, especially small liquid samples, can benefit a number of different fields. For instance, the agrochemical, pharmaceutical, environmental and cosmetic fields all have applications where large numbers of liquid samples containing chemicals are processed. Currently, many such fields use various strategies to reduce processing times, such as simplified chemistry, semi-automation, and robotics. While such strategies may improve the processing time for a particular type of liquid sample, process step or chemical reaction, such methods or apparatuses can seldom integrate the entire process, especially the generation or detection of chemical events in small volumes. Such apparatuses are also often limited in their application, since many of them are designed for, and dedicated to, a particular type of liquid sample or chemical reaction.

In most processes involving liquid samples, as the complexity of the liquid sample processing increases, the process time per sample increases. Although some very simple chemical reactions or liquid processing methods can achieve extremely high throughput rates, such as in the manufacturing of containerized liquids, complicated processing of liquids is typically several orders of magnitude slower. In some instances, the processing of liquid samples, such as in pharmaceutical arts, which usually demands complicated liquid processing for drug discovery, can obtain throughput rates of approximately 3,000 samples per day. This type of processing in general, however, uses liquid sample volumes on the order of 100 to 200 microliters, which often requires relatively large amounts of exotic and expensive reagents, and does not typically incorporate automated access to large stores of liquid reagents.

Consequently, there is a need to provide components, systems and methods for rapidly processing liquid samples at high throughput rates, particularly liquid samples of microliter volumes, one to ten microliters, to identify chemicals with useful activity. The multi-well platform of the present invention addresses these concerns and provides additional benefits as well.

SUMMARY

Figure 1A:
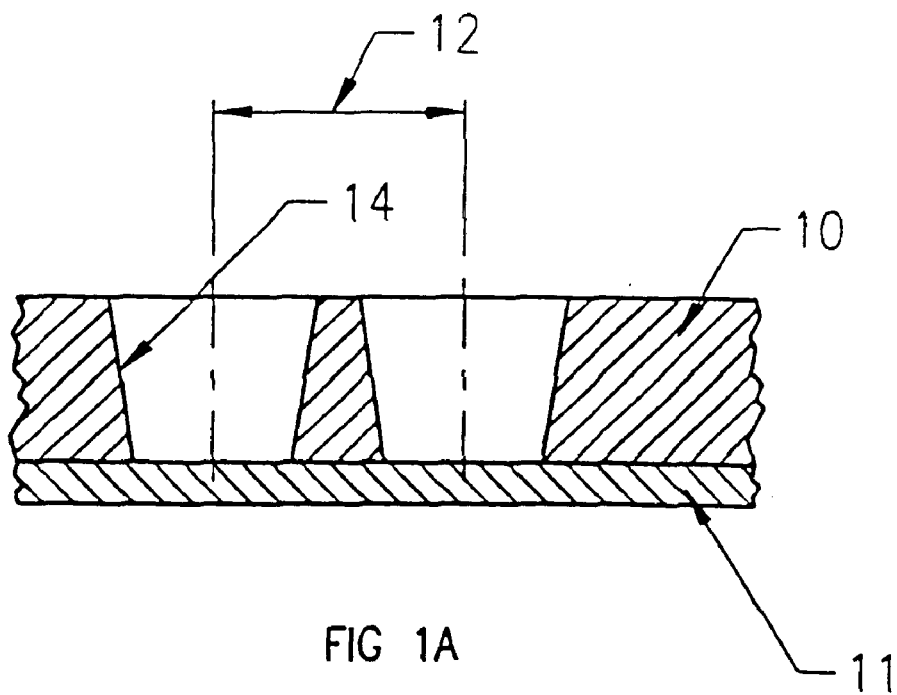
FIGS. 1A and 1B depict a cross-section of two embodiments of a multi-well platform.

One aspect of the present invention is a multi-well platform that has a plurality of wells within a frame. Each of these wells has a wall, which exhibits less fluorescence than a polystyrene wall of at least about 90 percent of the wall's thickness. Each well also has a bottom, which has a high transmittance portion and exhibits low background fluorescence. The thickness of the bottom can be less than about 450 microns, and can be as thin as about 20 to 100 micrometers and can exhibit superior optical properties compared to existing multi-well platforms. The optical properties of the multi-well platforms of the present invention can approach those of glass in the near-uv and visible spectra. The multi-well platform is particularly useful for measuring fluorescent events that can take place within the wells. The combination of the materials for the well wall and the thin bottom material, provides for particularly low fluorescent background. To make the multi-well platform compatible with robotics and automation equipment, it can have a footprint of a standard 96-well microtiter plate. To miniaturize and increase the throughput of such plates through automation equipment, the multi-well platform can have a high density of wells within that footprint. Furthermore, to reduce costs associated with valuable reagents, the wells of the multi-well platform can have a small volume, such as less than three microliters.

Another aspect of the present invention is a system for spectroscopic measurements, which includes a reagent for an assay and a multi-well platform for fluorescence measurements. The reagents can include, for example, cells, chemicals, solvents, buffers, and the like. The system can further comprise other elements, such as a detector to measure spectroscopic events within the wells, such as fluorescent events. Other elements can include robotics to retrieve and move the multi-well platform, robotics to dispense liquids into the multi-well platform, readers to measure events taking place within the wells of the multi-well platform, and informatics to store and analyze measurements obtained from reactions within the wells of the multi-well platform.

A further aspect of the present invention is a method for detecting the presence of an analyte in a sample contained in a multi-well platform. The method can be based on fluorescence, so that light emitted from a sample within a well of a multi-well platform is measured. The amount of fluorescence emitted from the well is indicative of a reaction within the well.

Another aspect of the present invention is a method for identifying a modulator of a biological process or target in a sample contained in a well of a multi-well platform. The method can use fluorescence, so that light emitted from the sample is detected. In practicing the method a biological process or target is contacted with a test chemical. This mixture, contained within a well of a multi-well platform, is excited with radiation of a first wavelength. Radiation of a second wavelength emitted from the sample is measured and can be indicative of the presence of a modulator within the sample. This method can be used to identify useful compounds; thus the present invention includes compounds identified by these methods.

A further aspect of the present invention is a method to identify a therapeutic by contacting a test chemical with a biological process or target. This mixture, contained within a well of a multi-well platform of the present invention, is excited with radiation of a first wavelength. Radiation of a second wavelength emitted from the sample is measured and can be indicative of the presence of a therapeutic within the sample. This method can be used to identify therapeutics; thus the present invention includes therapeutics identified by this method. A therapeutic identified using this method can be provided in a pharmaceutically acceptable carrier.

A further aspect of the present invention is a method of testing a therapeutic for therapeutic activity and toxicology. The method identifies a therapeutic using a method of the present invention. The identified therapeutic is then monitored for toxicity and efficacy in an in vitro or in vivo model.

DETAILED DESCRIPTION OF THE INVENTION

Definitions

Unless defined otherwise, all technical and scientific terms used herein have the same meaning as commonly understood by one of ordinary skill in the art to which this invention belongs. Generally, the nomenclature used herein, and the laboratory procedures in spectroscopy, drug discovery, cell culture, molecular genetics, plastic manufacture, polymer chemistry, diagnostics, amino acid and nucleic acid chemistry, and sugar chemistry described below, are those well known and commonly employed in the art. Standard techniques are typically used for preparation of plastics, signal detection, recombinant nucleic acid methods, polynucleotide synthesis, and microbial culture and transformation (e.g., electroporation, lipofection). The techniques and procedures are generally performed according to conventional methods in the art and various general references (see generally, Sambrook et al. Molecular Cloning: A Laboratory Manual, 2d ed. (1989) Cold Spring Harbor Laboratory Press, Cold Spring Harbor, N.Y., and Lakowicz, J. R. *Principles of Fluorescence Spectroscopy*, New York: Plenum Press (1983) for fluorescence techniques, which are incorporated herein by reference) which are provided throughout this document. Standard techniques are used for chemical syntheses, chemical analyses, and biological assays. As employed throughout the disclosure, the following terms, unless otherwise indicated, shall be understood to have the following meanings:

"Fluorescent donor moiety" refers to the radical of a fluorogenic compound that can absorb energy and is capable of transferring the energy to another fluorogenic molecule or part of a compound. Suitable donor fluorogenic molecules include, but are not limited to, coumarins and related dyes, xanthene dyes such as fluoresceins, rhodols, and rhodamines, resorufins, cyanine dyes, bimanes, acridines, isoindoles, dansyl dyes, aminophthalic hydrazides such as luminol and isoluminol derivatives, aminophthalimides, aminonaphthalimides, aminobenzofurans, aminoquinolines, dicyanohydroquinones, europium and terbium complexes, and related compounds.

"Quencher" refers to a chromophoric molecule or part of a compound which is capable of reducing the emission from a fluorescent donor when attached to the donor. Quenching may occur by any of several mechanisms including fluorescence resonance energy transfer, photoinduced electron transfer, paramagnetic enhancement of intersystem crossing, Dexter exchange coupling, and excitation coupling such as the formation of dark complexes.

"Acceptor" refers to a quencher that operates via fluorescence resonance energy transfer. Many acceptors can re-emit the transferred energy as fluorescence. Examples of these acceptors include coumarins and related fluorophores, xanthenes such as fluoresceins, rhodols, and rhodamines, resorufins, cyanines, difluoroboradiazaindacenes, and phthalocyanines. Other chemical classes of acceptors generally do not re-emit the transferred energy. Examples of these acceptors include indigos, benzoquinones, anthraquinones, azo compounds, nitro compounds, indoanilines, di- and triphenylmethanes.

"Binding pair" refers to two moieties (e.g. chemical or biochemical) that have an affinity for one another. Examples of binding pairs include antigen/antibodies, lectin/avidin, target polynucleotide/probe oligonucleotide, antibody/anti-antibody, receptor/ligand, enzyme/ligand and the like. "One member of a binding pair" refers to one moiety of the binding pair, such as an antigen or ligand.

"Dye," "pigment," or "chromophore" refer to a molecule or part of a compound that absorbs specific frequencies of light, including but not limited to ultraviolet light.

"Fluorophore" refers to a chromophore that fluoresces.

"Membrane-permeant derivative" refers a chemical derivative of a compound that has enhanced membrane permeability compared to an underivativized compound. Examples include ester, ether and carbamate derivatives. These derivatives are made better able to cross cell membranes, i.e. are membrane permeant, because hydrophilic groups are masked to provide more hydrophobic derivatives. Also, masking groups are designed to be cleaved from a precursor (e.g., fluorogenic substrate precursor) within the cell to generate the derived substrate intracellularly. Because the substrate is more hydrophilic than the membrane permeant derivative becomes trapped within the cells.

"Alkyl" refers to straight, branched, and cyclic aliphatic groups, generally of 1 to 8 carbon atoms, preferably 1 to 6 carbon atoms, and most preferably 1 to 4 carbon atoms. The term "lower alkyl" refers to straight and branched chain alkyl groups of 1 to 4 carbon atoms.

"Aliphatic" refers to saturated and unsaturated alkyl groups, generally of 1 to 10 carbon atoms, preferably 1 to 6 carbon atoms, and most preferably 1 to 4 carbon atoms.

"Heat fusion weld" refers to a weld induced by heat. The source of heat can be any source sufficient to promote some degree of attachment between two portions (separate or otherwise) of a material(s), including a chemical reaction, an external heat source (e.g., a heated platen, ultrasonic or air), or internal heating (e.g., radio frequency heating).

"Isolated polynucleotide" refers a polynucleotide of genomic, cDNA, or synthetic origin, or some combination there of, which by virtue of its origin the "isolated polynucleotide" (1) is not associated with the cell in which the "isolated polynucleotide" is found in nature, or (2) is operably linked to a polynucleotide which it is not linked to in nature.

"Isolated protein" refers a protein of cDNA, recombinant RNA, or synthetic origin, or some combination thereof, which by virtue of its origin the "isolated protein" (1) is not associated with proteins found it is normally found with in nature, or (2) is isolated from the cell in which it normally occurs, or (3) is isolated free of other proteins from the same cellular source, e.g. free of human proteins, or (4) is expressed by a cell from a different species, or (5) does not occur in nature. "Isolated naturally occurring protein" refers to a protein, which by virtue of its origin, the "isolated naturally occurring protein" (1) is not associated with proteins that it is normally found with in nature, or (2) is isolated from the cell in which it normally occurs, or (3) is isolated free of other proteins from the same cellular source, e.g. free of human proteins.

"Polypeptide" as used herein as a generic term to refer to native protein, fragments thereof, active fragments thereof, or analogs of a polypeptide sequence. Hence, native protein, fragments, and analogs are species of the polypeptide genus.

"Naturally-occurring" as used herein, as applied to an object, refers to the fact that an object can be found in nature. For example, a polypeptide or polynucleotide sequence that is present in an organism (including viruses) that can be isolated from a source in nature and which has not been intentionally modified by man in the laboratory is naturally-occurring.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

"Control sequence" refers to polynucleotide sequences which are necessary to effect the expression of coding and non-coding sequences to which they are ligated. The nature of such control sequences differs depending upon the host organism. In prokaryotes, such control sequences generally include promoter, ribosomal binding site, and transcription termination sequence. In eukaryotes, generally, such control sequences include promoters and transcription termination sequence. The term "control sequences" is intended to include, at a minimum, components whose presence can influence expression and can also include additional components whose presence is advantageous, for example, leader sequences and fusion partner sequences.

"Polynucleotide" refers to a polymeric form of nucleotides of at least 10 bases in length, either ribonucleotides or deoxynucleotides, or a modified form of either type of nucleotide. The term includes single, double, and triple stranded forms of DNA.

"Corresponds to" refers to a polynucleotide sequence that is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

"Polypeptide fragment" refers to a polypeptide that has an amino-terminal and/or carboxy-terminal deletion, but where the remaining amino acid sequence is usually identical to the corresponding positions in the naturally-occurring sequence deduced, for example, from a full-length cDNA sequence. Fragments typically can be at least 5, 6, 8, or 10 amino acids long, preferably at least 14 amino acids long, more preferably at least 20 amino acids long, usually at least 50 amino acids long, and can be at least 70 amino acids long.

"Plate" or "platform" refers to a multi-well platform, unless otherwise modified in the context of its usage.

"Cycloolefins" refer generally to cycloolefin polymers, unless otherwise modified in the context of its usage, and includes copolymers such as those so specified herein. "Cycloolefin copolymers" refer generally to cycloolefin copolymers, unless otherwise modified in the context of its usage.

"Modulation" refers to the capacity to either enhance or inhibit a functional property of biological activity or process (e.g., enzyme activity or receptor binding). Such enhancement or inhibition may be contingent on the occurrence of a specific event, such as activation of a signal transduction pathway, and/or may be manifest only in particular cell types.

The term "modulator" refers to a chemical compound (naturally occurring or non-naturally occurring), such as a biological macromolecule (e.g., nucleic acid, protein, non-peptide, or organic molecule), or an extract made from biological materials such as bacteria, plants, fungi, or animal (particularly mammalian) cells or tissues. Modulators are evaluated for potential activity as inhibitors or activators (directly or indirectly) of a "biological process or processes" (e.g., agonist, partial antagonist, partial agonist, antagonist, antineoplastic agents, cytotoxic agents, inhibitors of neoplastic transformation or cell proliferation, cell proliferation-promoting agents, and the like) by inclusion in screening assays described herein. The activity of a modulator may be known, unknown or partially known.

The term "test chemical" refers to a chemical to be tested by one or more screening method(s) of the invention as a putative modulator.

The term "analyte" refers to a chemical whose presence is to be tested by one or more screening method(s) of the invention.

The terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Various methods of labeling genes and polypeptides and glycoproteins are known in the art and may be used. Examples of labels include, but are not limited to, the following: radioisotopes (e.g., $^3H$, $^{14}C$, $^{35}S$, $^{125}I$, $^{131}I$), fluorescent labels (e.g., FITC, rhodamine, lanthanide phosphors), enzymatic labels (or reporter genes) (e.g., horseradish peroxidase, β-galactosidase, β-latamase, luciferase, alkaline phosphatase), chemiluminescent labels, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

"Fluorescent label" refers to incorporation of a detectable marker, e.g., by incorporation of a fluorescent moiety to a chemical entity that binds to a target or attachment to a polypeptide of biotinyl moieties, that can be detected by avidin (e.g., streptavidin containing a fluorescent label or enzymatic activity that can be detected by fluorescence detection methods) or other moieties. Various methods of labeling polypeptides and glycoproteins are known in the art and may be used. Examples of labels for polypeptides or other moieties include, but are not limited to dyes (e.g., FITC and rhodamine), intrinsically fluorescent proteins, and lanthanide phosphors. In some embodiments, labels are attached by spacer arms of various lengths to reduce potential steric hindrance.

"Reporter gene" refers to a nucleotide sequence encoding a protein that is readily detectable, either by its presence or activity, including, but not limited to, luciferase, green fluorescent protein, chloramphenicol acetyl transferase, β-galactosidase, secreted placental alkaline phosphatase, β-lactamase, human growth hormone, and other secreted enzyme reporters. Generally, reporter genes encode a polypeptide not otherwise produced by the host cell which is detectable by analysis of the cell(s), e.g., by the direct fluorometric, radioisotopic or spectrophotometric analysis of the cell(s) and preferably without the need to remove the cells for signal analysis of a well. Preferably, the gene encodes an enzyme that produces a change in fluorometric properties of the host cell that is detectable by qualitative, quantitative, or semi-quantitative function of transcriptional activation. Exemplary enzymes include esterases, phosphatases, proteases (tissue plasminogen activator or urokinase), and other enzymes whose function can be detected by appropriate chromogenic or fluorogenic substrates known to those skilled in the art. Proteins, particularly enzymes encoded by reporter genes can also be used as probes in biochemical assays, for instance after proper conjugation to either the target or a chemical entity that binds to the target.

"Transmittance" refers to the fraction of incident light that passes through a medium at a given wavelength. It can also be considered the ratio of radiant power transmitted through a medium to the radiant power incident on the medium at a particular wavelength.

"Fluorescent measurement" refers to the measurement of fluorescence from a sample, such as from a sample in a well of a multi-well platform, by any appropriate means known in the art or later developed.

"High transmittance portion" refers to a portion of a bottom of a well of a multi-well platform that can transmit radiation, such as light, in an assay, such as a fluorescence assay. Portion, in this context, refers to about 0.1% to 100%, preferably about 50% to greater than 90%, of the surface area of the bottom having high transmittance properties. Efficiently transmit radiation, in this context, refers to a transmittance of greater than about 1% of incident light.

"Footprint approximately that of a standard 96-well plate" refers to the dimensions of about 85.5 mm in width by about 127.5 mm in length, or the approximate dimensions of an industry standard multi-well plate.

"Chamfered wall" refers to the wall of a well having an angle of greater than 90° at least a portion between the top of the well to the bottom of the well. For example, the angle can be for the entire depth of the well, or only a portion of that depth. The angle is preferable from the top of the well towards the bottom of the well so that the area of the top of the well is larger than the area of the bottom of the well.

"Well center-to-center distance" refers to the distance between the center of one well to the center of a neighboring well.

"Optically opaque" refers to a material that presents a substantial barrier to the transmission of light. Substantial barrier, in this instance, refers to the ability of a material to block transmittance of greater than about 10% of incident light.

"Reflective coating" refers to a coating that renders a surface capable of reflecting radiation such as light. The reflective coating can be on the wall of a well and can reduce the amount of incident radiation that can be transmitted through the bottom. Such reflective coating is preferred when the wall is chamfered.

"Plurality of living cells" refers to one or more cells, wherein the cells can be prokaryotic, eukaryotic, or a mixture thereof.

"Target" refers to any biological entity, such as a protein, sugar, carbohydrate, nucleic acid, lipid, a cell or population of cells or an extract thereof, a vesicle, or any combination thereof.

Other chemistry terms herein are used according to conventional usage in the art, as exemplified by The McGraw-Hill Dictionary of Chemical Terms (ed. Parker, S., 1985), McGraw-Hill, San Francisco, incorporated herein by reference).

Introduction

During the course of miniaturizing and automating screening assays that use multi-well platforms, such as fluorescent assays, the inventors of the present invention realized that existing multi-well platforms were generally not suited for use with small assay volumes, such as a microliter or less. The inventors of the present invention discovered that when existing multi-well platforms were used for such small volumes, the assay became unpredictable and sometimes inoperable. Having discovered this previously unrecognized problem, the inventors of the present invention made multi-well platforms suitable for their purposes. The wall of a multi-well platform of the present invention exhibits less fluorescence than a polystyrene wall of at least about 90 percent of the wall's thickness. The bottom of the well can be about 450 micrometers thick, preferable about 20 to 100 micrometers thick, and can exhibit optical properties superior to existing multi-well platforms. The multi-well platforms of the represent invention can have a footprint compatible with robotics, and automation, and instrumentation. Furthermore, to miniaturize and increase the throughput of these plates through such automation equipment, the multi-well platform of the present invention can have a high density of wells in such a footprint, such as between about 6 and 5000 wells.

As a non-limiting introduction to the breadth of the invention, the invention includes several general and useful aspects, including:

1) multi-well platforms that are useful for performing fluorescent measurements,
2) a system for spectroscopic measurements using (1),
3) a method for detecting the presence of an analyte in a sample contained in (1),
4) a method for identifying a modulator of a biological process or target in a sample using (1),
5) a composition identifying a composition using (1) and (3) or (4),
6) a method of testing a therapeutic for therapeutic activity using (1), and
7) a therapeutic identified by (6).

These aspects of the invention, as well as others described herein, can be achieved by using the methods, devices, and compositions of matter described herein. To gain a full appreciation of the scope of the invention, it will be further recognized that various aspects of the invention can be combined to make desirable embodiments of the invention.

Multi-Well Platforms

The multi-well platforms of the present invention are well suited for use in fluorescent based assays, but can be used for any appropriate purpose. These multi-well platforms comprise a frame, wherein said wells are disposed in said frame. The frame can be of any thickness, such as between about 0.5, 1, 2, 3, or 5 millimeters and 2, 3, 5, 10 or 20 millimeters. The frame can be made of any material, such as polymers, such as polystyrene or cycloolefins, or other materials, such as glass or quartz. The frame can be of any shape, and typically defines the footprint of the multi-well platform.

The bottom of the frame can be substantially flat, meaning in this instance that the bottom of the frame does not have additional structures, such as means to form a band of opaque material in the bottom when the frame and bottom are sealed together (see, U.S. Pat. No. 5,319,436 (Mann et al.)). Such bands of opaque material are preferred when the wall is chamfered, however, the present invention is useful with or without such bands of opaque material. The bottom of the frame can also include structures such as pins, grooves, flanges or other known structures or those developed in the future to orient the multi-well platform on another structure, such as a detector or another platform.

The multi-well platform can have a footprint of any shape or size, such as square, rectangular, circular, oblong, triangular, kidney, or other geometric or non-geometric shape. The footprint can have a shape that is substantially similar to the footprint of existing multi-well platforms, such as the standard 96-well microtiter plate, whose footprint is approximately 85.5 mm in width by 127.75 mm in length or other sizes that represent a current or future industry standard (see T. Astle, Standards in Robotics and Instrumentation, J. of Biomolecular Screening, Vol. 1 pages 163–168 (1996)). Other standard footprints are presented in Table 1. Multi-well platforms of the present invention having this footprint can be compatible with robotics and instrumentation, such as multi-well platform translocators and readers as they are known in the art.

TABLE 1

| Mfrs Cat. # | Mfrs Name | Outside Dimensions | | | Wells | | | | |
|---|---|---|---|---|---|---|---|---|---|
| | | Length | Width | Height | Wells | Shape | Color | Material | Bottom |
| | AGTC | 128.118 | 85.319 | 41.148 | | | | Styrene | 1 ml |
| | AIM | 127.762 | 85.598 | 41.504 | | | | Styrene | 1 ml |
| | AIM | 127.635 | 85.141 | 40.945 | | | | Propylene | 1 ml |
| | Beckman | 127.93 | 85.55 | 41.84 | 96 | round | clear | Styrene | Round |
| | Beckman | 127.93 | 85.55 | 41.84 | 96 | round | translucent | Propylene | Round |
| 373660 | Beckman | 127.787 | 85.573 | 14.224 | | | clear | Styrene | Flat |
| 25870 | Corning/Costar | 127.68 | 85.12 | 14.2 | 96 | round | clear | Styrene | Flat(bezel) |
| 35207 | Corning/Costar | 127.61 | 85.166 | 14.224 | | | clear | Styrene | Flat |
| 35205 | Corning/Costar | 127.33 | 85.014 | 14.224 | | | clear | Styrene | U-Bottom |
| | Corning/Costar | 127.6 | 85.2 | 14.3 | 96 | round | clear | Styrene | Cone |
| 7000003 | Corning/Costar | 127.1 | 85.3 | 14.3 | 96 | round | black | Styrene | Flat |
| 7000004 | Corning/Costar | 127.6 | 85.47 | 14.2 | 96 | round | black | Styrene | Flat |
| 7000008 | Corning/Costar | 126.7 | 84.62 | 14.45 | 96 | round | translucent | Propylene | Round |
| 7000010 | Corning/Costar | 127.83 | 85.42 | 14.53 | 96 | round | clear | Styrene | Flat |
| 35203 | Corning/Costar | 127.508 | 85.319 | 14.224 | | | clear | Styrene | Flat |

TABLE 1-continued

| Mfrs Cat. # | Mfrs Name | Outside Dimensions | | | Wells | | | |
|---|---|---|---|---|---|---|---|---|
| | | Length | Width | Height | Wells | Shape | Color | Material | Bottom |
| 35202 | Corning/Costar | | 85.42 | 14.326 | | | clear | Styrene | Flat A/2 |
| 35190 | Dynatech | 127.889 | 85.649 | 14.173 | | | clear | Styrene | Flat |
| 35189 | Dynatech | 127.838 | 85.522 | 14.097 | | | clear | Styrene | V-Bottom |
| 35194 | Evergreen | 127.483 | 85.344 | 14.376 | | | clear | Styrene | Flat |
| 35192 | Evergreen | 127.483 | 85.217 | 14.275 | | | clear | Styrene | U-Bottom |
| 35191 | Evergreen | 127.432 | 85.268 | 14.3 | | | clear | Styrene | V-Bottom |
| 35197 | Falcon | 127.381 | 85.471 | 14.351 | | | clear | Styrene | Flat |
| 7000017 | Genetix | 128.28 | 86.31 | 10.17 | 384 | round | clear | Styrene | Flat |
| 35188 | Immulon | 127.406 | 85.344 | 14.402 | | | clear | Styrene | Flat |
| 35176 | Interlab | 127.914 | 85.852 | 13.665 | | | clear | Styrene | V-Bottom |
| | Iwaki | 127.279 | 85.065 | 14.021 | | | | Styrene | Flat |
| 35181 | LabSystems | 127.838 | 85.598 | 15.291 | | | black | Propylene | Flat |
| 35187 | MicroFluor | 127.406 | 85.217 | 12.224 | | | white | Propylene | Flat |
| 35184 | MicroFluor | 127.508 | 85.42 | 14.275 | | | black | Propylene | Flat |
| 35183 | MicroFluor | 127.533 | 85.42 | 14.224 | | | white | Propylene | Flat A/2 |
| 35185 | MicroLite | 127.584 | 85.369 | 14.148 | | | white | Propylene | Flat |
| 35186 | MicroLite 2 | 127.635 | 85.471 | 14.199 | | | white | Propylene | Flat |
| | Millipore | 128.016 | 85.75 | 14.859 | | | white | Propylene | Flat |
| | Millipore | 127.813 | 85.598 | 14.605 | | | clear | Sryrene | Flat |
| 35177 | NBT | 127.838 | 85.598 | 14.3 | | | clear | Styrene | U-Bottom |
| 7000001 | Nunc | 127.6 | 83.7 | 14.4 | 96 | round | clear | Styrene | Flat |
| 7000006 | Nunc | 127.7 | 85.6 | 14.5 | 384 | square | clear | Styrene | Flat |
| 63765 | Nunc | 127.559 | 85.573 | 14.351 | | | clear | Styrene | Flat |
| 35201 | Nunc | 127.432 | 85.344 | 14.097 | | | clear | Styrene | U-Bottom |
| 35200 | Nunc | 126.314 | 84.379 | 14.351 | | | | Propylene | U-Bottom |
| 35199 | Nunc | 127.305 | 85.395 | 14.402 | | | clear | Styrene | V-Bottom |
| 35210 | Packard | 127.762 | 85.471 | 14.275 | | | white | Propylene | GF/B |
| 35209 | Packard | 127.965 | 85.776 | 14.351 | | | white | Propylene | GF/C |
| 35203 | Pall | 127.635 | 85.598 | 14.325 | | | white | Propylene | Flat |
| 7000005 | Polyfiltronics | 127.5 | 85.8 | 44.03 | 96 | square | translucent | Propylene | Round |
| 7000009 | Polyfiltronics | 127.09 | 85.12 | 30.43 | 96 | round | translucent | Propylene | Filter |
| 7000011 | Polyfiltronics | 127.3 | 85.25 | 16 | 96 | round | translucent | Propylene | Cone |
| 7000012 | Polyfiltronics | 127.8 | 85.69 | 9.56 | 384 | round | translucent | Propylene | Cone |
| 35175 | Polyfiltronics | 127.787 | 85.552 | 15.24 | | | white | Propylene | Flat |
| 35174 | Polyfiltronics | 127.483 | 85.547 | 15.189 | | | black | Propylene | Flat |
| 35173 | Polyfiltronics | 127.991 | 85.7 | 15.24 | | | white | Propylene | Clear-flat |
| 35179 | Polyfiltronics | 127.559 | 85.344 | 14.351 | | | white | Propylene | GF/B |
| 35180 | Polymetrics | 127.533 | 85.369 | 14.097 | | | translucent | Propylene | Deep V |
| | Sumilon | 127.33 | 85.395 | 14.503 | | | | Styrene | Flat |
| 35178 | Tilertek | 127.381 | 85.319 | 14.224 | | | clear | Styrene | Flat |

Each well comprises a wall having less fluorescence than polystyrene wall of 100 to 70% of the wall's thickness, preferably at least 90 percent of the wall's thickness. These determinations can be made using fluorescent detection methods well known in the art, such as determining the fluorescence of appropriate sheets of the materials being compared or as described herein.

Typically, wells will be arranged in two-dimensional linear arrays on the multi-well platform. However, the wells can be provided in any type of array, such as geometric or non-geometric arrays. The number of wells can be no more than 864 wells, or greater than 864 wells, on a standard multi-well platform footprint. Larger numbers of wells or increased well density can also be easily accomplished using the methods of the claimed invention. Other commonly used number of wells include 1536, 3456, and 9600. The number of wells can be between about 50, 100, 200, 500, 700, 800 or 1000 wells and 150, 250, 600, 800, 1000, 2000, 4000 5000, or 10000 wells. Preferably, the number of wells can be between about 50 and 10000, more preferable between about 800 and 5000, and most preferably between about 900 and 4000. The number of wells can be a multiple of 96 within these ranges, preferably the square of an integer multiplied by 96.

Well volumes typically can vary depending on well depth and cross sectional area. Well volumes can range between about 0.5, 1, 5, 10, 25, 50, 75, 100 or 200 microliter and about 5, 15, 40, 80, 100, 200, 500, or 1000 microliters. Preferably, the well volume is between about 500 nanoliters and 500 microliters, more preferably between about 1 microliter and 200 microliter, and most preferably between about 0.5 microliters and 10 microliters.

Wells can be made in any cross sectional shape (in plan view) including, square, round, hexagonal, other geometric or non-geometric shapes, and combinations (intra-well and inter-well) thereof. Wells can be made in any cross sectional shape (in vertical view) including shear vertical or chamfered walls, wells with flat or round bottoms, conical walls with flat or round bottoms, and curved vertical walls with flat or round bottoms, and combinations thereof.

As shown in FIG. 1A, the walls can be chamfered (e.g. having a draft angle) 14. Chamfered walls can have an angle between about 1, 2, 3, 4, or 5 degrees and about 2, 3, 4, 5, 6, 7, 8, 10, or 20 degrees. Preferably, the angle is between about 1 and 10 degrees, more preferably between about 2 and 8 degrees, and most preferable between about 3 and 5 degrees.

As shown in FIG. 1, the wells can be placed in a configuration so that the well center-to well-center distance 12 can be between about 0.5, 1, 2, 5, or 10 millimeters and about 1, 2, 5, 10, 20, 50, or 100 millimeters. The wells can be placed in any configuration, such as a linear-linear array, or geometric patterns, such as hexoginal patterns. The well-to-well distance can be about 9 mm divided by an integer between 1 and 10. Typically, the multi-well plate has wells with a well-center-to-well-center distance of less than about 2.5 mm, preferably less than 2 mm and some times less than about 1 mm. Smaller well-center to well-center distances are preferred for smaller volumes.

The wells can have a depth between about 0.5, 1, 2, 3, 4, 5, 10, 20, or 50 millimeters and about 5, 10, 20, 50, or 100 millimeters. Preferably, the well depth is between about 1 millimeter and 100 millimeters, more preferably between about 2 millimeters and 50 millimeters, and most preferably between about 3 millimeters and 20 millimeters.

The wells can have a diameter (when the wells are circular) or maximal diagonal distance (when the wells are not circular) between about 0.2, 0.5, 0.7, 1, 5, 10, or 50 millimeters and about 1, 5, 10, 20, 50, or 100 millimeters. Preferably, the well diameter is between about 0.5 and 100 millimeters, more preferably between about 1 and 50 millimeters, and most preferably, between about 2 and 20 millimeters.

The wells of the multi-well platform can comprise an optically opaque material that can interfere with the transmission of radiation, such as light, through the wall of a well or bottom of a well. Such optically opaque materials can reduce the background associated with optical detection methods. Optically opaque materials can be any known in the art or later developed, such as dyes, pigments or carbon black. The frame can be made of an optically opaque material, or the walls or bottom, or both, can be coated with an optically opaque material. The optically opaque material can prevent radiation from passing from one well to another, to prevent cross-talk between wells, so that the sensitivity and accuracy of the assay is increased. The optically opaque material can also be reflective, such as those known in the art, such as thin metal layers, mirror coatings, or mirror polish. Optically opaque materials can be coated onto any surface of the multi-well platform, or be an integral part of the frame or bottom as they are manufactured. Optically opaque material can prevent the transmittance of between about 100% to about 50% of incident light, preferably between about 80% and greater than 95%, more preferably greater than 99%.

Since most measurements will not typically require light to pass through the wall of the well, materials such as polymers can include pigments to darken well walls or absorb light. Such application of pigments will help reduce background fluorescence. Pigments can be introduced by any means known in the art, such as coating or mixing during the manufacture of the material or multi-well platform. Pigment selection can be based on a mixture of pigments to dampen all background inherent to the polymer, or a single pigment or ensemble of pigments selected to filter or absorb light at desired wavelengths. Pigments can include carbon black. Such pigmentation is generally not desired in embodiments where light is directed through the well wall as a method for illuminating the contents of the well.

Each well also comprises a bottom 11 having a high transmittance portion and having less fluorescence than a polystyrene-bottom of at least about 90 percent of said bottom's thickness. This property can be determined by comparing the fluorescence of an appropriate control bottom material with the fluorescence of a test material. These procedures can be performed using well known methods. The thickness of the bottom can vary depending on the overall properties required of the plate bottom that may be dictated by a particular application. Preferably, the bottom is a plate or film as these terms are known in the art. Such properties include the amount of intrinsic fluorescence, rigidity, breaking strength, and manufacturing requirements relating to the material used in the plate. Well bottom layers typically have a thickness between about 10, 15, 20, 50, 100, 200, or 300 micrometers and about 20, 50, 100, 200, 300, 450, 500, or 1000 micrometers. Preferably, the well bottom has a thickness between about 10 micrometers and 450 micrometers, more preferably between about 15 micrometers and 300 micrometers, and most preferably between about 20 micrometers and 100 micrometers.

Figure 1B:
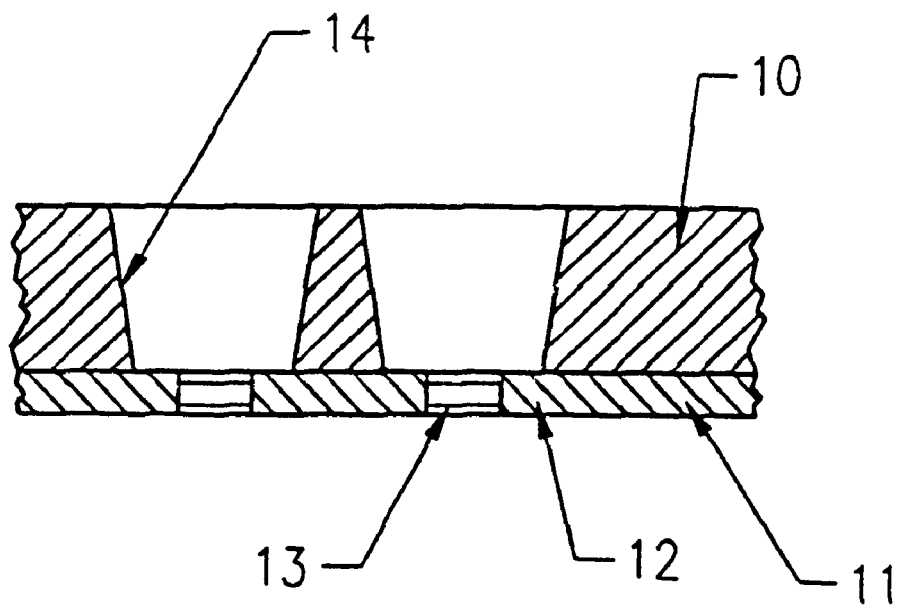

The bottom of a well can have a high transmittance portion, typically meaning that either all or a portion of the bottom of a well can transmit light. As shown in FIG. 1B, the bottom can have an optically opaque portion 12 and a high transmittance portion 13 of any shape, such as circular, square, rectangular, kidney shaped, or other geometric or non-geometric shape or combinations thereof. In applications of the invention that can utilize focused light, the bottom, or a portion thereof, can be used to form a lens. Lens will vary in thickness and curvature depending on the application, such as convex or concave in shape.

The bottom can produce about 200 percent or less of the fluorescence compared to glass of 100 microns thickness at excitation wavelengths between about 290, 300, 310, 320, or 350 to about 300, 340, 370, 400, or 420 nm and at emission wavelengths between about 290, 300, 350, 400, or 500 and about 400, 600, 800, or 1000 nm.

Preferably, the bottom of the multi-well platform can be substantially flat, e.g. having a surface texture between about 0.001 mm and 2 mm, preferably between about 0.01 mm and 0.1 mm (see, Surface Roughness, Waviness, and Lay, Am. Soc. of Mech. Eng. #ANSI ASME B46.1-2985 (1986)). If the bottom is not substantially flat, then the optical quality of the bottom and wells can decrease because of altered optical and physical properties of one or both. Furthermore, the bottom of the frame can be substantially flat within the meaning set forth in this paragraph.

One feature of the preferred multi-well platform of the present invention is their low intrinsic fluorescence. Bottom layers comprising cycloolefin typically produces about 100 to 200 percent or less of the fluorescence compared to glass of about 130 to 170 micrometers in thickness. Glass, particularly fused silica, is typically used a "gold standard" for comparison of relative fluorescence. Fluorescence and relative fluorescence can be measured using any reliable techniques known or developed in the art, preferably the techniques described herein are used. Preferably, the glass standard used herein to show the surprisingly low fluorescence of polymers such as cycloolefin is used as a standard. Preferably, the bottom typically produces about 100 to 200 percent or less of the fluorescence compared to glass of about 0.085 to 0.13 millimeters (85 to 130 micrometers) thick (for glass slides, see Thomas Scientific, MicroCover Glasses, No. 0, product No. 6661 -B40). The amount of intrinsic fluorescence can be dictated, in part, by the layer thickness. In some applications that can tolerate particularly thin bottoms, such as applications where the bottom does not require significant structural strength, layer thickness can be quite thin (e.g., 20 to 80 microns) in order to reduce fluorescence arising from the bottom. The thinness of a bottom is usually also balanced against the difficulty of uniformly welding or generating thinner layers in manufacturing processes. The low relative fluorescence of the multi-well platform is usually present at excitation wavelengths between about 300 to 400 nm and at emission wavelengths between about 350 to 800 nm.

The bottom or wells can also include at least one or a plurality of living cells. The cells can be prokaryotic, such as bacteria, or eukaryotic, such as plant cells, mammalian cells, or yeast cells. The cells can include more than one type of cell, such as a mixture of different mammalian cells, or a mixture of prokaryotic and eukaryotic cells. Such embodiments are useful for cell based assays described herein and for growing cells using culture methods. The multi-well platforms of the invention can include a coating (e.g., polylysine or fibronectin) to enhance attachment of cells. Coatings can also include at least one substrate for a cell adhesion molecule, such as integrins. Such substrates are known in the art.

The multi-well platform of the present invention can include coatings or surface modifications to facilitate various applications of the plate as described herein and known or developed in the relevant art. Coatings can be introduced using any suitable method known in the art, including printing, spraying, radiant energy, ionization techniques or dipping. Surface modifications can also be introduced by appropriately derivatizing a polymer or other material, such as glass or quartz, before, during, or after the multi-well platform is manufactured and by including an appropriate derivatized polymer or other material in the bottom layer or frame. The derivatized polymer or other material can then be reacted with a chemical moiety that is used in an application of the plate. Prior to reaction with a chemical moiety, such polymer or other material can then provide either covalent or non-covalent attachment sites on the polymer or other material. Such sites in or on the polymer or other material surface can be used to attach moieties, such as assay components (e.g., one member of a binding pair), chemical reaction components (e.g., solid synthesis components for amino acid or nucleic acid synthesis), and cell culture components (e.g., proteins that facilitate growth or adhesion). Examples of derivatized polymers or other materials include those described by U.S. Pat. No. 5,583,211 (Coassin et al.) and others known in the art or later developed. Particularly preferred embodiments are based on polyethylene and polypropylene derivatives that can be included as cycloolefin copolymers.

The materials for manufacturing the multi-well platform will typically be polymeric, since these materials lend themselves to mass manufacturing techniques. However, other materials can be used to make the frame or bottom of the multi-well platform, such as glass or quartz. The frame and bottom can be made of the same or different materials and the bottom can comprise polystyrene, or another material. Preferably, polymers are selected that have low fluorescence or other properties using the methods described herein. The methods herein can be used to confirm that selected polymers possess the desire properties. Polymeric materials can particularly facilitate plate manufacture by molding methods known in the art and developed in the future, such as insert or injection molding.

The multi-well platform of the present invention can be made of one or more pieces. For example, the frame and bottom can be made as one discrete piece. Alternatively, the frame can be one discrete piece, and the bottom can be a second discrete piece, which are combined to form a multi-well platform. In this instance, the frame and bottom can be attached to each other by sealing means, such as adhesives, sonic welding, heat welding, melting, insert injection molding or other means known in the art or later developed. The frame and bottom can be made of the same or different material. For example, the frame can be made of a polymer, and the bottom made of polystyrene, glass, or quartz.

Uses for multi-well platforms are known in the relevant arts and include diagnostic assays, chemical or biochemical binding assays, filtration assays, chemical synthesis sites, storage sites, and the like. Such uses can also be applied to the multi-well platforms of the present invention. It will be recognized that some types of multi-well platforms for spectroscopic measurements can often be used for other multi-well platform applications. Typically, a multi-well platform is used for detecting a signal from a sample. Different types of signal measurements are discussed herein.

The multi-well platform of the present invention can also include at least one orienting structure, such as holes, indentations, flanges, grooves, notches, or other such structures to orient the multi-well platform in robotics or instrumentation.

Figure 2:
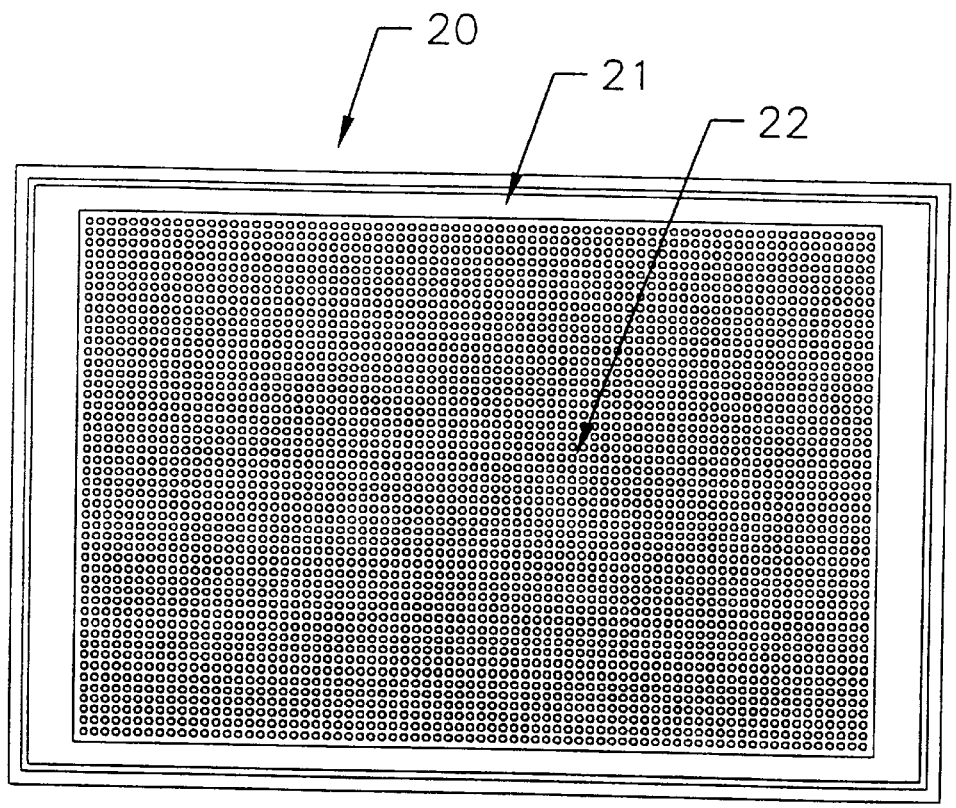
FIG. 2 depicts a top plain view of one embodiment of a multi-well platform.

As shown in FIG. 2, the multi-well platform 20 of the present invention can also include at least one recessed groove 21. As shown in FIG. 2, the recessed groove can surround the matrix of wells 22. The recessed groove can be filled with a fluid, such as water or buffer, to provide a humid atmosphere for the wells. The multi-well platform can also comprise an identification structure, such as a barcode, numbering or lettering.

Figure 3:
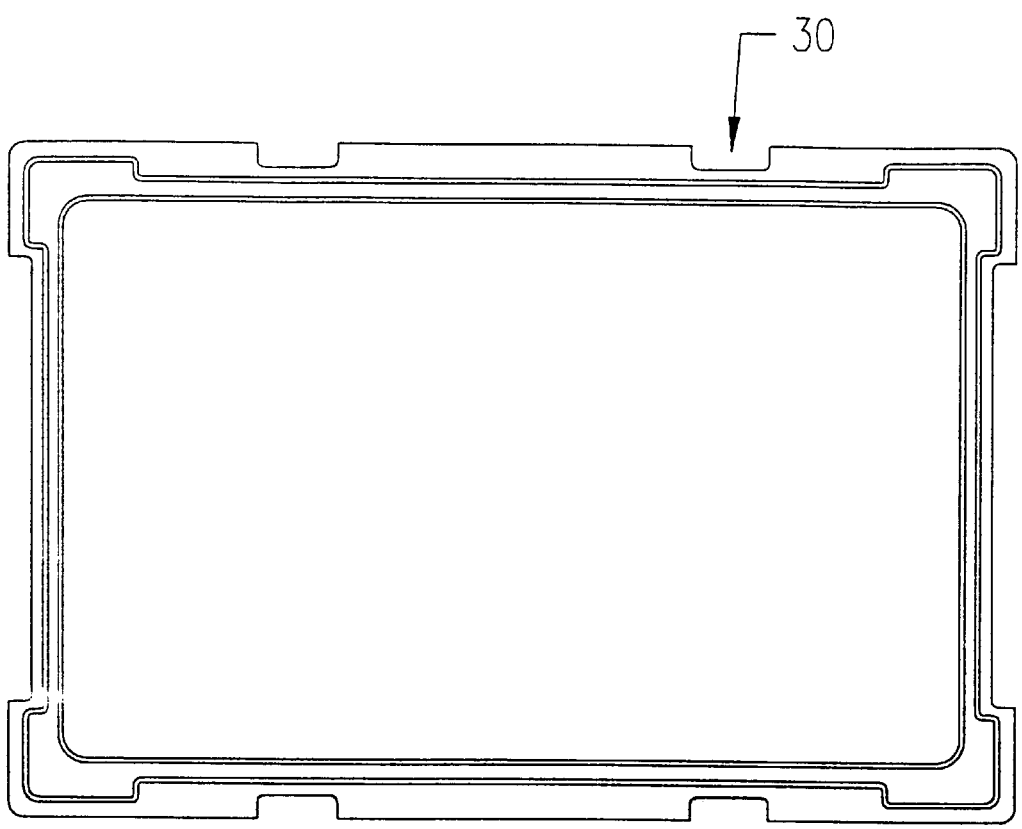
FIG. 3 depicts a top plain view of one embodiment of a covering means.

As shown in FIG. 3, the multi-well platform can also include a structure 30 to cover at least a portion of the multi-well platform. This structure can cover the entire multi-well platform, such as the case of a polymeric bag, or can be a ridged cover or flexible film that covers at least a portion of the upper face of the multi-well plate which can include at least a portion of a recessed groove, which can comprise a fluid to maintain a humid environment within the wells. Alternatively, this structure can form a seal by being immersed in a fluid within the at least on recessed groove. The cover can be a water vapor permeable barrier made of materials known in the art or a non-aqueous barrier, such as mineral oil, silicon oil, or paraffin wax. When the multi-well platform and a ridged covering means are engaged, the distance between the top of the frame and the bottom of the covering means is preferably between about 0.1, 0.5, 1, or 5 millimeters and 0.5, 1, 5, or 10 millimeters, but any distance is useful in the present invention. As the well volume decreases, the effects of evaporation become greater, and the need for such covering means can increase. This structure can also comprise an identification structure, such as a barcode, numbering or lettering.

Figure 4:
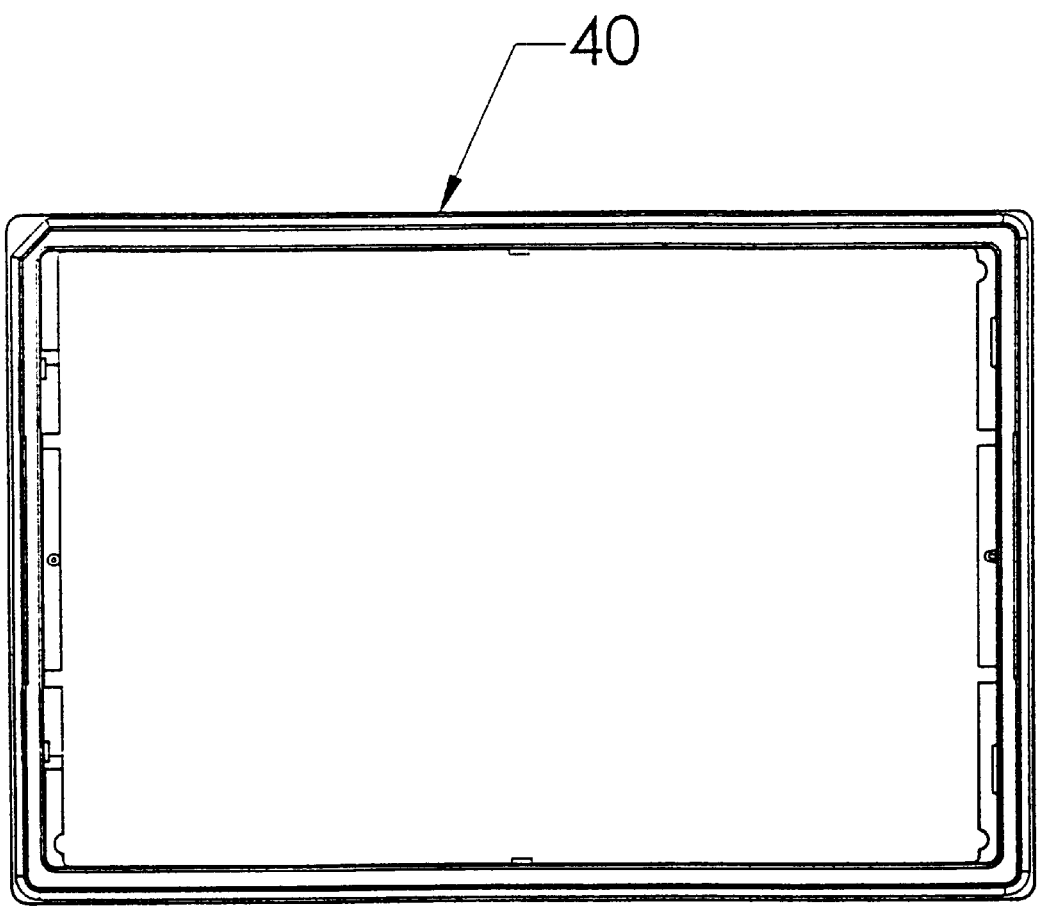
FIG. 4 depicts a top plain view of one embodiment of a holding means.

As shown in FIG. 4, the multi-well platform of the present invention can be held in a structure 40 to hold the multi-well platform in a substantially planar configuration to prevent optical distortion of the wells of the multi-well platform of the present invention. The multi-well platform can have a flatness between about 0.001 mm and 2 mm, preferably between about 0.001 mm and 2 mm, or between about 0.01 mm and 0.1 mm (see, Am. Soc. of Mech. Eng. #ASME B46.1-1985, supra, (1986)). This structure holding can comprise at least one orienting structure that can match the orienting structure of the multi-well platform. Preferably, the bottom or top of the wells are not obscured by this holding structure so that the wells can be observed while held by the holding structure by, for example, optical devices. This holding structure can also comprise numbering or lettering to indicate a grid matrix anywhere on the structure 50, and can also include identification marks, such a bar-codes, to identify the multi-well platform housed therein. This structure can also comprise a window or an opening to allow identification marks, such as bar codes, on the multi-well plate to be observed and read by, for example, a bar-code reader.

The multi-well platform, covering structure, and holding structure can be provided separately, or in any combination, in a container, such as a hermetically sealed container as is known in the art. The contents of the hermetically sealed container can be provided sterile. The contents within the hermetically sealed container can be sterilized using, for example, ionizing radiation as is known in the art.

Materials, Selection Criteria and Testing

This section describes materials, selection criteria, and rapid tests to facilitate choosing a material for the multi-well plates described herein.

Materials

The present inventors conducted extensive research on different polymers in search of polymers that offer the appropriate properties for detecting spectroscopic signals, particularly fluorescence signals. Although any suitable material can be used, such as polymers or other materials such as glass or quartz, some of the materials used in the present invention have not been used in the commercially available multi-well platforms listed in Table 1. Surprisingly, these materials offer exceptional properties, including low intrinsic fluorescence, which was demonstrated herein for the first time.

The methods described herein to identify cycloolefin copolymers as low fluorescent materials can be used to screen other materials, such as other polymers and other materials such as glasses and quartz, in a variety of configurations, such as in plates, sheets, or films, to determine if they possess desirable optical or fluorescent properties. Thus, these teachings should not be construed to be limited to cycloolefins.

Polymers that are compatible with cycloolefin can be used in regions of the multi-well platform in physical contact with cycloolefin. In some embodiments, the frame can be manufactured with a material other than a cycloolefin polymer and the cycloolefin bonded, welded or otherwise fused to the second material. Polymers with glass transition temperatures suitable for heat induced fusion with cycloolefin can be selected for manufacturing the wells and other portions of the plate.

Typically, cycloolefins can be used as films, plates, or resins to make various embodiments of present invention. Resins and films based on cycloolefin polymers can be used in various manufacturing processes known in the relevant art and described herein. Selection criteria for cycloolefin films or resins are described more fully below.

Suitable cycloolefins for many embodiments of the present invention include those described in U.S. Pat. Nos. 5,278,238 (Lee B. L. et al); 4,874,808 (Minami et al); 4,918,133 (Moriya et al); 4,935,475 (Kishimura et al); 4,948,856 (Minchak et al); 5,115,052 (Wamura et al); 5,206,306 (Shen); 5,270,393 (Sagane et al); 5,272,235 (Wakatsuru et al); 5,278,214 (Moriya et al); 5,534,606 (Bennett et al); 5,532,030 (Hirose et al); 4,689,380 (Nahm et al); and 4,899,005 (Lane et al). Cycloolefins available from Hoechst (Summerville, N.J.) are preferred, especially cycloolefin (e.g., cyclopentene, cyclohexane, and cycloheptene) and their polyethylene copolymers, as well as the thermoplastic olefin polymers of amorphous structure (TOPAS line).

Multilayer laminates are preferred when multiple functional requirements are difficult to obtain from a single laminate (e.g., layer or film). The properties of transmittance, rigidity, heat sealability, fluorescence, moisture penetration can be blended by the use of films of differing resins. Blended resins known in the art and developed in the future can be used when multilaminate films or blended resins have properties consistent with those of the present invention. For example, U.S. Pat. No. 5,532,030 (Hirose et al) describes the manufacture of certain cycloolefin films, both single and multilaminate, that can be adapted for use in the devices described herein. The present invention includes multilaminates of any suitable material, such as polymers and other materials, such as glass or quartz.

Selection Criteria and Testing

Desirable properties for materials used in the present invention will vary depending on the type of multi-well plate desired. Generally, the materials are selected to yield a final product with low fluorescence, high transmittance, sufficient rigidity to resist deformity, and to allow for substantially single plane (especially for spectroscopic embodiments), good chemical inertness to, for example, DMSO, relatively low cytotoxicity, low water absorption, heat resistance/deflection up to about 150° C., and resistance to acids and bases. Starting materials with good molding properties are particularly desirable.

Fluorescence of the materials or final product can be readily measured. Such measurements proceed rapidly and a number of plates or films (e.g., 20 to 80 films), or prototype products, can be rapidly tested within a matter of hours or days, usually less than a one person week. Consequently, films or resins used to make final products can rapidly be selected for the desired properties that are important in a particular application. The fluorescence measurements can be used as described herein or those known in the art, so long as the measurements are comparable (or better) in sensitivity to the measurements described herein. A standard reference point for relative fluorescence, such as the standard described herein, is particularly useful for comparing different cycloolefins and for determining their applicability to certain applications. Relative fluorescence properties described herein are particularly desirable. Similarly, transmittance of films, plates, or final products can be measured using techniques known in the relevant art.

In the final product, layer thicknesses of generally, about 20 to 500 micrometers, are most likely to impart the properties desirable for use in the devices described herein, especially low fluorescence and high transmittance. Although thinner or thicker films, such as about 10 to 1,500 micrometers, can be used in applications where the demands for extremely low fluorescence and high transmittance films are less stringent, or when there is little loss in the desired properties as a function of film thickness. Preferably, film thickness is between about 30 to 200 micrometers for multi-well platform applications, and more preferably between about 50 to 150 micrometers, and most preferably between about 80 to 100 micrometers. Preferably, film thickness is between about 30 to 600 micrometers for scaffolding applications where the film typically contributes to a structural function in the device that usually demands more strength or rigidity, and more preferably between about 100 to 500 micrometers, and most preferably between about 120 to 200 micrometers. Preferably, film thickness is between about 75 to 600 micrometers for the thinner regions of injection molded applications where the film typically contributes to a structural function, more preferably between about 100 to 500 micrometers and most preferably between about 120 to 200 micrometers. Film thickness refers to the thickness of the film used (or material thickness). Layer thickness is generally about 100 to 200 percent of film thickness, preferably about 100 to 150 percent of film thickness and more preferably about 100 to 125 percent of film thickness.

In the final product, breaking stresses (Kg/cm$^2$ at 22° C.) of generally, about 400 to 3,000 Kg/cm$^2$ are most likely to impart the properties desirable for use in the devices described herein, especially rigid devices of low fluorescence and high transmittance. Although weaker or stronger films, such as about 200 to 3,500 Kg/cm², can be used in different applications based on the demands for breaking strength of the device. For example, the breaking strength of the film, generally need not be as great for the bottoms of multi-well platforms as compared to applications where the film is part of the frame in a multi-well platform. Preferably, breaking stress is between about 500 to 2,000 Kg/cm² for multi-well plate applications, and more preferably between about 800 to 1,600 Kg/cm² and most preferably between about 900 to 1,400 Kg/cm². Preferably, breaking stress for platform/scaffolding applications is about 15 to 60 percent higher than for multi-well platform applications. Breaking stresses can be measured by standard techniques as known in the art. In addition to cycloolefins, materials such as other polymers such as polystyrene, polycarbonate, polypropylene, poly-methyl pentene, copolymers of and of the above-mentioned polymers, or any other polymer appropriate for an intended use of a multi-well platform of the present invention, or other materials, such as glass or quartz, can be used to make the frame or bottom of a multi-well platform of the present invention.

Manufacturing Methods

The present invention includes a process for making cycloolefin based multi-well platforms. Other methods appropriate for other materials, such as other polymers or other materials such as glasses or quartz, are readily apparent to those skilled in the art based on the properties of the material or materials selected.

A variety of processes can be used, including heat welding, insert molding, injection molding and other processes described herein and known in the art. One process comprises heat welding a frame to a bottom exhibiting low fluorescence and high transmittance, such as a cycloolefin copolymer. Processes typically use a cycloolefin copolymer selected from the group of cyclopentene polyethylene copolymer, cyclohexane polyethylene copolymer, and cycloheptene polyethylene copolymer. The process can alternatively, or optionally, comprise the step of exposing the layer and the polymer to a sufficient amount of radio frequency energy to promote internal heating of the layer and the polymer, or ultrasonic welding. Alternatively the process can entail heating the layer and the polymer that forms the wells to about 320° C. for a sufficient amount of time to allow fusion of the polymers. Pressure can be applied to enhance the welding process (e.g., about 100 and 1,000 psi of pressure to the layer and the polymer for low pressure processes using low viscosity monomer solutions and about 10,000 to 25,000 psi for high pressure processes such as insert molding).

In another embodiment, the invention provides for a process for making multi-well plates by injection molding or insert molding. Injection molding techniques known in the art or developed in the future can be applied. The process comprises insert molding at least a well to a bottom of the well of the multi-well plate, wherein the bottom is a cycloolefin copolymer. Using this method, cycloolefin films can be heat fused to the supporting structure (e.g., the frame) to make a multi-well platform. The entire frame or platform can also be made of a cycloolefin. Inserting molding can be performed between about 195 and 350° C. degrees, preferably resins are heated to 260° to 320° C. Pressures used are typically between 10,000 and 25,000 psi and preferably about 15,000 to 22,000 psi.

Methods for preparing of cycloolefins and their polymers have been described. Other methods and cycloolefins were described in U.S. Pat. Nos. 4,002,815; 4,069,376; 4,110,528; 4,262,103 and 4,380,617 (by Robert J. Minchak and co-workers). A number of catalysts can be used in the manufacture of cycloolefins as known in the art or developed in the future and can be used to manufacture materials for various embodiments of the present invention. Such catalysts include those described in U.S. Pat. Nos. 5,278,238 (Lee et al) and 5,278,214 (Moriya et al). Regardless of the exact type of catalyst system utilized, cycloolefin monomers can be polymerized in the presence of a catalyst and the ethylene based functional copolymers to make embodiments of the invention suitable for injection molding. Polymerization can carried out preferably in bulk. Bulk polymerization such as reaction injection molding (RIM), liquid injection molding (LIM), reinforced reaction injection molding (RRIM), and resin transfer molding (RTM) and combinations thereof are known to the art well as those techniques developed in the future. Bulk polymerization is polymerization conducted in the absence of a solvent or a diluent. Reaction injection molding is a type of bulk polymerization wherein a monomer in a liquid state is transferred or is injected into a mold where polymerization of the monomer takes place in the presence of a catalyst system. RIM is not conventional injection molding for melt polymers and is readily distinguishable therefrom.

RIM is a low pressure, one-step or one-shot, mix and injection of two or more liquid components into a closed mold where rapid polymerization occurs resulting in a molded plastic product. RIM differs from conventional injection molding in a number of important aspects. Conventional injection molding is conducted at pressures of about 10000 to 20,000 psi in the mold cavity by melting a solid resin and conveying it into a mold maintained at a temperature less than the melt temperature of the resin. At an injection temperature of about 150° to 350° C., viscosity of the molten resin in conventional injection molding process is generally in the range of 50,000 to 1,000,000 and typically about 200,000 cps. In the injection molding process, solidification of the resin occurs in about 10 to 90 seconds, depending on the size of the molded product, following which, the molded product is removed from the mold. There is no chemical reaction occurring in a conventional injection molding process when the resin is introduced into a mold.

In a RIM process, the viscosity of the materials fed to a mix chamber is about 1 to 10,000 cps, preferably 1 to about 1500 cps, at injection temperatures varying from room temperature to about 100° C. for different cycloolefin monomer systems. Mold temperatures in a RIM process are in the range of about 50° C. to 150° C. and pressures in the mold are generally in the range of about 50 to 150 psi. At least one component in the RIM formulation is a monomer that is polymerized to a polymer in the mold. The main distinction between conventional injection molding and RIM resides in the fact that in RIM, a chemical reaction is initiated on mixing, with optional heating, and is completed in the mold to transform monomers to a polymeric state. For practical purposes, the chemical reaction must take place rapidly in less than about 2 minutes.

Conventional injection molding can also be used to make various embodiments of the invention. The term injection molding refers to both conventional injection molding and the other types of injection molding described herein and known or developed in the art.

A LIM process is similar to a RIM system except that generally an impingement head is not utilized. Instead, a simple mixer is utilized such as a static mixer, an agitating mixer, and the like. Moreover, in a LIM system, the injection molding cycle is carried out over a longer period of time and thus the chemical reaction can take place in a period of up to about 5 or 10 minutes.

Various reinforcing particles can also be utilized, that is injected with the solution when utilizing either the RIM or the LIM process. As a practical manner, the RIM process is not always suitable and hence reinforced particles are generally utilized only in a LIM process, that is a reinforced liquid injection molding process. Another alternative is to utilize a mat that already exists in a mold, for example a fiberglass mat, or the like. Accordingly, such systems are called RMRIM, RMLIM, or RTM. Due to the reaction cure times as well as injection molding times, the RMLIM system is generally preferred for some operations, RMRIM or RTM for others.

Hence, the blends or alloys of cycloolefins and suitable copolymers can he utilized in any of the above noted bulk polymerization systems as well as variations thereof. In as much as the above systems are generally conventional or known to the art as well as to the literature, they have not been discussed in detail, but rather briefly discussed herein for purposes or brevity.

U.S. Pat. No. 4,426,502 to Minchak describes bulk (e.g., RIM) polymerization of cycloolefins using a modified co-catalyst with a catalyst whereby polymerization of the cycloolefin monomers can be conducted in absence of a solvent or a diluent. The alkylaluminum halide co-catalyst is modified by pre-reacting it with an alcohol or an active hydroxy-containing compound to form an alkyoxyalkylaluminum halide or an aryloxyalk-ylaluminum halide that is then used in the polymerization reaction. The pre-reaction can be accomplished by using oxygen, an alcohol, or a phenol. Such modification of the co-catalyst results in lowering of its reducing potential of the catalyst.

Regardless of whether the halide metathesis or the halogen-free metathesis catalyst system is utilized, the reaction rate is generally slowed down by utilization of the above-described alcohols. Thus, depending if little or no alcohol is utilized, the halide metathesis catalyst system can cure the various cycloolefins in a matter of minutes and even seconds. If high amounts of alcohol are utilized, the cure can be a matter of hours and even days.

It is important to lower the reducing power of the co-catalyst of either metathesis system in order to make such bulk polymerization reactions practical. When a monomer diluted with unmodified alkylaluminum co-catalyst is mixed with a monomer-diluted catalyst to polymerize a cycloolefin, the reaction is very rapid. In such systems, the polymerization is usually unacceptable because polymer formed at the interfaces or the two streams during intermingling prevents thorough mixing and results in poor conversions. Modifying the co-catalyst by pre-reaction with hydroxy-containing materials reduces the activity of the co-catalyst to the point where adequate mixing of the liquid components can occur and acceptable polymer products can be produced. Sometimes, a cycloolefinic monomer will contain various impurities that naturally reduce the activity of the co-catalyst. In such cases, it is not necessary to add active hydroxy-containing materials to reduce the activity of the co-catalyst. With the modified co-catalyst, mixing or the cycloolefins, and other components, can be carried out at lower temperatures, such as room temperature, without immediately initiating polymerization. The co-catalyst can be formulated to allow a reasonable pot life at room temperature and thermal activation in the mold of the mixed liquid components. The co-catalyst can also be formulated to give mixing initiated RIM systems.

When utilizing a bulk polymerization method, the blend of the cycloolefin monomers and the ethylene-based functional copolymers as well as the catalyst and any optional additives therein can be added to a bulk polymerizing mold having a temperature well below the Tg of the polymerized cycloolefin polymers. This is especially desirable since the reaction is usually exotheromic and can result in a temperature increase of the mold up to about 120° C. The final mold temperature is thus from about 50° C. to about 200° C., generally from about 50° C. to about 150° C., and preferably from about 50° C. to about 90° C. Of course, such temperatures will vary depending upon the specific type of catalyst system utilized, the specific type of cycloolefin monomers, and the like. When utilizing the catalyst systems described herein above, the cycloolefin monomer and ethylene-based functional co-polymer mixture has a good shelf life that is up to about 24 hours. Should longer times be desirable, the catalyst system is not added to the mixture but kept separate. Thus, upon the point in time of carrying out the polymerization of the cycloolefin monomers, the catalyst system is added to the mixture and polymerized in bulk. A preferred method of polymerization includes the above noted RIM method.

A System for Spectroscopic Measurements

The present invention is a system for spectroscopic measurement, comprising: a reagent for an assay, and a device comprising at least one multi-well platform of the present invention, and a second platform to hold said multi-well platform for detecting a signal from a sample. The system can further comprise a detector. In this context, a reagent for an assay includes any reagent useful to perform biochemical or biological in vitro or in vivo testing procedures, such as, for example, buffers, proteins, carbohydrates, lipids, nucleic acids, active fragments thereof, organic solvents such as DMSO, chemicals, analytes, therapeutics, compositions, cells, antibodies, ligands, and the like. In this context, an active fragment is a portion of a reagent that has substantially the activity of the parent reagent. The choice of a reagent depends on the type of assay to be performed. For example, an immunoassay would include an immuno-reagent, such as an antibody, or an active fragment thereof.

The present invention is directed to systems and methods that utilize automated and integratable workstations for detecting the presence of an analyte and identifying modulators or chemicals having useful activity. The present invention is also directed to chemical entities and information (e.g., modulators or chemical or biological activities of chemicals) generated or discovered by operation of workstations of the present invention.

The present invention includes automated workstations that are programmably controlled to minimize processing times at each workstation and that can be integrated to minimize the processing time of the liquid samples from the start to finish of the process. Typically, a system of the present invention would include: A) a storage and retrieval module comprising storage locations for storing a plurality of chemicals in solution in addressable chemical wells, a chemical well retriever and having programmable selection and retrieval of the addressable chemical wells and having a storage capacity for at least 100,000 the addressable wells, B) a sample distribution module comprising a liquid handler to aspirate or dispense solutions from selected the addressable chemical wells, the chemical distribution module having programmable selection of, and aspiration from, the selected addressable chemical wells and programmable dispensation into selected addressable sample wells (including dispensation into arrays of addressable wells with different densities of addressable wells per centimeter squared), C) a sample transporter to transport the selected addressable chemical wells to the sample distribution module and optionally having programmable control of transport of the selected addressable chemical wells (including adaptive routing and parallel processing), D) a reaction module comprising either a reagent dispenser to dispense reagents into the selected addressable sample wells or a fluorescent detector to detect chemical reactions in the selected addressable sample wells, and a data processing and integration module.

The present invention can be used with systems and methods that utilize automated and integratable workstations for identifying modulators, pathways, chemicals having useful activity and other methods described herein. Such systems are described generally in the art (see, U.S. Pat. Nos. 4,000,976 to Kramer et al. (issued Jan. 4, 1977), 5,104,621 to Pfost et al. (issued Apr. 14, 1992), 5,125,748 to Bjornson et al. (issued Jun. 30, 1992), 5,139,744 to Kowalski (issued Aug. 18, 1992), 5,206,568 Bjornson et al. (issued Apr. 27, 1993), 5,350,564 to Mazza et al. (Sep. 27, 1994), 5,589,351 to Harootunian (issued Dec. 31, 1996), and PCT Application Nos: WO 93/20612 to Baxter Deutschland GMBH (published Oct. 14, 1993), WO 96/05488 to McNeil et al. (published Feb. 22, 1996) and WO 93/13423 to Agong et al. (published Jul. 8, 1993).

The storage and retrieval module, the sample distribution module, and the reaction module are integrated and programmably controlled by the data processing and integration module. The storage and retrieval module, the sample distribution module, the sample transporter, the reaction module and the data processing and integration module are operably linked to facilitate rapid processing of the addressable sample wells., Typically, devices of the invention can process at least 100,000 addressable wells in 24 hours. This type of system is described in U.S. Ser. No. 08/858,016 by Stylli et al., filed May 16, 1997, entitled "Systems and method for rapidly identifying useful chemicals in liquid samples," which is incorporated herein by reference.

If desired, each separate module is integrated and programmably controlled to facilitate the rapid processing of liquid samples, as well as being operably linked to facilitate the rapid processing of liquid samples.

In one embodiment the invention provides for a reaction module that is a fluorescence detector to monitor fluorescence. The fluorescence detector is integrated to other workstations with the data processing and integration module and operably linked with the sample transporter. Preferably, the fluorescence detector is of the type described herein and can be used for epi-fluorescence. Other fluorescence detectors that are compatible with the data processing and integration module and the sample transporter, if operable linkage to the sample transporter is desired, can be used as known in the art or developed in the future. For some embodiments of the invention, particularly for plates with 96, 192, 384 and 864 wells per plate, detectors are available for integration into the system. Such detectors are described in U.S. Pat. No. 5,589,351 (Harootunian), U.S. Pat. No. 5,355,215 (Schroeder), and PCT patent application WO 93/13423 (Akong). Each well of a multi-well platform can be "read" sequentially. Alternatively, a portion of, or the entire plate, can be "read" simultaneously using an imager, such as a Molecular Dynamics Fluor-Imager 595 (Sunnyvale, Calif.).

Fluorescence Measurements

It is recognized that different types of fluorescent monitoring systems can be used to practice the invention with fluorescent probes, such as fluorescent dyes or substrates. Preferably, systems dedicated to high throughput screening, e.g., 96-well or greater microtiter plates, are used. Methods of performing assays on fluorescent materials are well known in the art and are described in, e.g., Lakowicz, J. R., *Principles of Fluorescence Spectroscopy*, New York: Plenum Press (1983); Herman, B., Resonance Energy Transfer Microscopy, in: *Fluorescence Microscopy of Living Cells in Culture, Part B. Methods in Cell Biology*, vol. 30, ed. Taylor, D. L. & Wang, Y.-L., San Diego: Academic Press (1989), pp. 219–243; Turro, N. J., *Modern Molecular Photochemistry*, Menlo Park: Benjamin/Cummings Publishing Col, Inc. (1978), pp. 296–361 and the Molecular Probes Catalog (1997), OR, USA.

Fluorescence in a sample can be measured using a detector described herein or known in the art for multi-well platforms. In general, excitation radiation from an excitation source having a first wavelength, passes through excitation optics. The excitation optics causes the excitation radiation to excite the sample. In response, fluorescent probes in the sample emit radiation that has a wavelength that is different from the excitation wavelength. Collection optics then collect the emission from the sample. The device can include a temperature controller to maintain the sample at a specific temperature while it is being scanned. According to one embodiment, a multi-axis translation stage (e.g., a dedicated X,Y positioner) moves a multi-well platform holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation.

Preferably, FRET (fluorescence resonance energy transfer) is used as a way of monitoring probes in a sample (cellular or biochemical). The degree of FRET can be determined by any spectral or fluorescence lifetime characteristic of the excited construct, for example, by determining the intensity of the fluorescent signal from the donor, the intensity of fluorescent signal from the acceptor, the ratio of the fluorescence amplitudes near the acceptor's emission maxima to the fluorescence amplitudes near the donor's emission maximum, or the excited state lifetime of the donor. For example, cleavage of the linker increases the intensity of fluorescence from the donor, decreases the intensity of fluorescence from the acceptor, decreases the ratio of fluorescence amplitudes from the acceptor to that from the donor, and increases the excited state lifetime of the donor.

Preferably, changes in signal are determined as the ratio of fluorescence at two different emission wavelengths, a process referred to as "ratioing." Differences in the absolute amount of probe (or substrate), cells, excitation intensity, and turbidity or other background absorbances between addressable wells can affect the fluorescence signal. Therefore the ratio of the two emission intensities is a more robust and preferred measure of activity than emission intensity alone.

A ratiometric fluorescent probe system can be used with the invention. For instance the reporter system described in PCT publication WO96/30540 (Tsien and Zlokarnik) has significant advantages over existing reporters for gene integration analysis, as it allows sensitive detection and isolation of both expressing and non-expressing single living cells. This assay system uses a non-toxic, non-polar fluorescent substrate that is easily loaded and then trapped intracellularly. Cleavage of the fluorescent substrate by β-lactamase yields a fluorescent emission shift as substrate is converted to product. Because the β-lactamase reporter readout is ratiometric, it is unique among reporter gene assays in that it controls variables such as the amount of substrate loaded into individual cells. The stable, easily detected, intracellular readout simplifies assay procedures by eliminating the need for washing steps, which facilitates screening with cells using the invention.

Methods for Detecting the Presence an Analyte in a Sample

A method of the present invention uses targets for detecting the presence of an analyte, such as chemicals that are useful in modulating the activity of a target, in a sample. Typically, as discussed below targets can be proteins such as cell surface proteins or enzymes. A biological process or a target can be assayed in either biochemical assays (targets free of cells), or cell based assays (targets associated with a cell). This method can also be used to identify a modulator of a biological process or target in a sample. This method detects the presence of an analyte in a sample contained in a multi-well platform of the present invention by detecting light emitted from the sample. The method comprises the steps of: exciting at least one sample with radiation of a first wavelength, wherein at least one sample suspected of containing an analyte is placed into at least one well of a multi-well platform of the present invention, which can contain a biological process or target. The sample and biological process or target can be contacted within the well, or outside of the well and later placed within the well. The emission of radiation of a second wavelength emitted from the sample is measured, wherein the amount of radiation of a second wavelength measured indicates the presence or absence of the analyte in the sample.

Targets can be cells, which may be loaded with ion or voltage sensitive dyes to report receptor or ion channel activity, such as calcium channels or N-methyl-D-aspartate (NMDA) receptors, GABA receptors, kainate/AMPA receptors, nicotinic acetylcholine receptors, sodium channels, calcium channels, potassium channels excitatory amino acid (EAA) receptors, nicotinic acetylcholine receptors. Assays for determining activity of such receptors can also use agonists and antagonists to use as negative or positive controls to assess activity of tested chemicals. In preferred embodiments of automated assays for identifying chemicals that have the capacity to modulate the function of receptors or ion channels (e.g., agonists, antagonists), changes in the level of ions in the cytoplasm or membrane voltage will be monitored using an ion-sensitive or membrane voltage fluorescent indicator, respectively. Among the ion-sensitive indicators and voltage probes that may be employed, are those disclosed in the Molecular Probes 1997 Catalog, herein incorporated by reference.

Other methods of the present invention concern determining the activity of receptors. Receptor activation can sometimes initiate subsequent intracellular events that release intracellular stores of calcium ions for use as a second messenger. Activation of some G-protein-coupled receptors stimulates the formation of inositol triphosphate (IP3 a G-protein coupled receptor second messenger) through phospholipase C-mediated hydrolysis of phosphatidylinositol, Berridge and Irvine (1984), Nature 312: 315–21. IP3 in turn stimulates the release of intracellular calcium ion stores. Thus, a change in cytoplasmic calcium ion levels caused by release of calcium ions from intracellular stores can be used to reliably determine G-protein-coupled receptor function. Among G-protein-coupled receptors are muscarinic acetylcholine receptors (mAChR), adrenergic receptors, serotonin receptors, dopamine receptors, angiotensin receptors, adenosine receptors, bradykinin receptors, metabotropic excitatory amino acid receptors and the like. Cells expressing such G-protein-coupled receptors may exhibit increased cytoplasmic calcium levels as a result of contribution from both intracellular stores and via activation of ion channels, in which case it may be desirable, although not necessary, to conduct such assays in calcium-free buffer, optionally supplemented with a chelating agent such as EGTA, to distinguish fluorescence response resulting from calcium release from internal stores.

Other assays can involve determining the activity of receptors which, when activated, result in a change in the level of intracellular cyclic nucleotides, e.g., cAMP, cGMP. For example, activation of some dopamine, serotonin, metabotropic glutamate receptors and muscarinic acetylcholine receptors results in a decrease in the cAMP or cGMP levels of the cytoplasm. Furthermore, there are cyclic nucleotide-gated ion channels, e.g., rod photoreceptor cell channels and olfactory neuron channels (see, Altenhofen, W. et al. (1991) Proc. Natl. Acad. Sci U.S.A. 88: 9868–9872 and Dhallan et al. (1990) Nature 347: 184–187) that are permeable to cations upon activation by binding of cAMP or cGMP. In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. Cells for this type of assay can be made by co-transfection of a host cell with DNA encoding a cyclic nucleotide-gated ion channel and DNA encoding a receptor (e.g., certain metabotropic glutamate receptors, muscarinic acetylcholine receptors, dopamine receptors, serotonin receptors, and the like), which, when activated, cause a change in cyclic nucleotide levels in the cytoplasm.

Any cell expressing a protein target in sufficient quantity for measurement in a cellular assay can be used with the invention. Cells endogenously expressing a protein can work as well as cells expressing a protein from heterologous nucleic acids. For example, cells may be transfected with a suitable vector encoding one or more such targets that are known to those of skill in the art or may be identified by those of skill in the art. Although essentially any cell which expresses endogenous ion channel or receptor activity may be used, when using receptors or channels as targets it is preferred to use cells transformed or transfected with heterologous DNAs encoding such ion channels and/or receptors so as to express predominantly a single type of ion channel or receptor. Many cells that can be genetically engineered to express a heterologous cell surface protein are known. Such cells include, but are not limited to, baby hamster kidney (BHK) cells (ATCC No. CCL10), mouse L cells (ATCC No. CCLI.3), Jurkats (ATCC No. TIB 152) and 153 DG44 cells (see, Chasin (1986) Cell. Molec. Genet. 12: 555) human embryonic kidney (HEK) cells (ATCC No. CRL1573), Chinese hamster ovary (CHO) cells (ATCC Nos. CRL9618, CCL61, CRL9096), PC12 cells (ATCC No. CRL17.21) and COS-7 cells (ATCC No. CRL1651). Preferred cells for heterologous cell surface protein expression are those that can be readily and efficiently transfected. Preferred cells include Jurkat cells and HEK 293 cells, such as those described in U.S. Pat. No. 5,024,939 and by Stillman et al. (1985) Mol. Cell. Biol. 5: 2051–2060.

Exemplary membrane proteins include, but are not limited to, surface receptors and ion channels. Surface receptors include, but are not limited to, muscarinic receptors, e.g., human M2 (GenBank accession #M16404); rat M3 (GenBank accession #M16407); human M4 (GenBank accession #M16405); human M5 (Bonner, et al., (1988) Neuron 1, pp. 403–410); and the like. Neuronal nicotinic acetylcholine receptors include, but are not limited to, e.g., the human $\alpha_2$, $\alpha_3$, and $\beta_2$, subtypes disclosed in U.S. Ser. No. 504,455 (filed Apr. 3, 1990, which is hereby expressly incorporated by reference herein in its entirety); the human $\alpha_5$ subtype (Chini, et al. (1992) Proc. Natl. Acad. Sci. U.S.A. 89: 1572–1576), the rat $\alpha_2$ subunit (Wada, et al. (1988) Science 240, pp. 330–334); the rat $\alpha_3$ subunit (Boulter, et al. (1986) Nature 319, pp. 368–374); the rat $\alpha_4$ subunit (Goldman, et al. (1987) Cell 48, pp. 965–973); the rat $\alpha_5$ subunit (Boulter, et al. (1990) J. Biol. Chem. 265, pp. 4472–4482); the chicken $\alpha_7$ subunit (Couturier et al. (1990) Neuron 5: 847–856); the rat $\beta_2$ subunit (Deneris, et al. (1988) Neuron 1, pp. 45–54) the rat $\beta_3$ subunit (Deneris, et al. (1989) J. Biol. Chem. 264, pp. 6268–6272); the rat $\beta_4$ subunit (Duvoisin, et al. (1989) Neuron 3, pp. 487–496); combinations of the rat $\alpha$ subunits, $\beta$ subunits and a and p subunits; GABA receptors, e.g., the bovine n, and p, subunits (Schofield, et al. (1987) Nature 328, pp. 221–227); the bovine n, and a, subunits (Levitan, et al. (1988) Nature 335, pp. 76–79); the $\gamma$-subunit (Pritchett, et al. (1989) Nature 338, pp. 582–585); the p, and p, subunits (Ymer, et al. (1989) EMBO J. 8, pp. 1665–1670); the 6 subunit (Shivers, B. D. (1989) Neuron 3, pp. 327–337); and the like. Glutamate receptors include, but are not limited to, e.g., rat GluR1 receptor (Hollman, et al. (1989) Nature 342, pp. 643–648); rat GluR2 and GluR3 receptors (Boulter et al. (1990) Science 249:1033–1037; rat GluR4 receptor (Keinanen et al. (1990) Science 249: 556–560); rat GluR5 receptor (Bettler et al. (1990) Neuron 5: 583–595) g rat GluR6 receptor (Egebjerg et al. (1991) Nature 351: 745–748); rat GluR7 receptor (Bettler et al. (1992) neuron 8:257–265); rat NMDAR1 receptor (Moriyoshi et al. (1991) Nature 354:31–37 and Sugihara et al. (1992) Biochem. Biophys. Res. Comm. 185:826–832); mouse NMDA e1 receptor (Meguro et al. (1992) Nature 357: 70–74); rat NMDAR2A, NMDAR2B and NMDAR2C receptors (Monyer et al. (1992) Science 256: 1217–1221); rat metabotropic mGluR1 receptor (Houamed et al. (1991) Science 252: 1318–1321); rat metabotropic mGluR2, mGluR3 and mGluR4 receptors (Tanabe et al. (1992) Neuron 8:169–179); rat metabotropic mGluR5 receptor (Abe et al. (1992) J. Biol. Chem. 267: 13361–13368); and the like. Adrenergic receptors include, but are not limited to, e.g., human p1 (Frielle, et al. (1987) Proc. Natl. Acad. Sci. 84, pp. 7920–7924); human $\alpha_2$ (Kobilka, et al. (1987) Science 238, pp. 650–656); hamster $\beta_2$ (Dixon, et al. (1986) Nature 321, pp.75–79); and the like. Dopamine receptors include, but are not limited to, e.g., human D2 (Stormann, et al. (1990) Molec. Pharm. 37, pp. 1–6); mammalian dopamine D2 receptor (U.S. Pat. No. 5,128,254); rat (Bunzow, et al. (1988) Nature 336, pp. 783–787); and the like. NGF receptors include, but are not limited to, e.g., human NGF receptors (Johnson, et al. (1986) Cell 47, pp. 545–554); and the like. Serotonin receptors include, but are not limited to, e.g., human 5HT1a (Kobilka, et al. (1987) Nature 329, pp. 75–79); serotonin 5HT1C receptor (U.S. Pat. No. 4,985,352); human 5HT1D (U.S. Pat. No. 5,155,218); rat 5HT2 (Julius, et al. (1990) PNAS 87, pp.928–932); rat 5HT1c (Julius, et al. (1988) Science 241, pp. 558–564); and the like.

Ion channels include, but are not limited to, calcium channels comprised of the human calcium channel $\alpha_2$ $\beta$ and/or $\gamma$-subunits disclosed in commonly owned U.S. application Ser. Nos. 07/745,206 and 07/868,354, filed Aug. 15, 1991 and Apr. 10, 1992, respectively, the contents of which are hereby incorporated by reference; (see also, WO89/09834; human neuronal $\alpha_2$ subunit); rabbit skeletal muscle a1 subunit (Tanabe, et al. (1987) Nature 328, pp. 313-E318); rabbit skeletal muscle $\alpha_2$ subunit (Ellis, et al. (1988) Science 241, pp. 1661–1664); rabbit skeletal muscle p subunit (Ruth, et al. (1989) Science 245, pp. 1115–1118); rabbit skeletal muscle $\gamma$ subunit (Jay, et al. (1990) Science 248, pp. 490–492); and the like. Potassium ion channels include, but are not limited to, e.g., rat brain (BK2) (McKinnon, D. (1989) J. Biol Chem. 264, pp. 9230–8236); mouse brain (BK1) (Tempel, et al. (1988) Nature 332, pp. 837–839); and the like. Sodium ion channels include, but are not limited to, e.g., rat brain I and II (Noda, et al. (1986) Nature 320, pp. 188–192); rat brain III (Kayano, et al. (1988) FEBS Lett. 228, pp. 187-1.94); human II (ATCC No. 59742, 59743 and Genomics 5: 204–208 (1989); chloride ion channels (Thiemann, et al. (1992), Nature 356, pp. 57–60 and Paulmichl, et al. (1992) Nature 356, pp. 238–241), and others known or developed in the art.

Intracellular receptors may also be used as targets, such as estrogen receptors, glucocorticoid receptors, androgen receptors, progesterone receptors, and mineralocorticoid receptors, in the invention. Transcription factors and kinases can also be used as targets, as well as plant targets.

Various methods of identifying activity of chemical with respect to a target can be applied, including: ion channels (PCT publication WO 93/13423) and intracellular receptors (PCT publication WO 96/41013, U.S. Pat. No. 5,548,063, U.S. Pat. No. 5,171,671, U.S. Pat. No. 5,274,077, U.S. Pat. No. 4,981,784, EP 0 540 065 A1, U.S. Pat. No. 5,071,773, and U.S. Pat. No. 5,298,429). All of the foregoing references are herein incorporated by reference in their entirety.

If the analyte is present in the sample, then the target will exhibit increased or decreased fluorescence. Such fluorescence can be detected using the methods of the present invention by exciting the sample with radiation of a first wavelength, which excites a fluorescent reporter in the sample, which emits radiation of a second wavelength, which can be detected. The amount of the emission is measured, and compared to proper control or background values. The amount of emitted radiation that differs from the background and control levels, either increased or decreased, correlates with the amount or potency of the analyte in the sample. Standard curves can be determined to make the assay more quantitative.

Testing a Therapeutic for Therapeutic Activity and Toxicology

The present invention also provides a method for testing a therapeutic for therapeutic activity and toxicology. A therapeutic is identified by contacting a test chemical suspected of having a modulating activity of a biological process or target with a biological process or target in a multi-well platform of the present invention. If the sample contains a modulator, then the amount of a fluorescent reporter product in the sample, such as inside or outside of the cell, will either increase or decrease relative to background or control levels. The amount of the fluorescent reporter product is measured by exciting the fluorescent reporter product with an appropriate radiation of a first wavelength and measuring the emission of radiation of a second wavelength emitted from said sample. The amount of emission is compared to background or control levels of emission. If the sample having the test chemical exhibits increased or decreased emission relative to that of the control or background levels, then a candidate modulator has been identified. The amount of emission is related to the amount or potency of the therapeutic in the sample. Such methods are described in, for example, Tsien (PCT/US90/04059) The candidate modulator can be further characterized and monitored for structure, potency, toxicology, and pharmacology using well known methods.

The structure of a candidate modulator identified by the invention can be determined or confirmed by methods known in the art, such as mass spectroscopy. For putative modulators stored for extended periods of time, the structure, activity, and potency of the putative modulator can be confirmed.

Depending on the system used to identify a candidate modulator, the candidate modulator will have putative pharmacological activity. For example, if the candidate modulator is found to inhibit T-cell proliferation (activation) in vitro, then the candidate modulator would have presumptive pharmacological properties as an immunosuppressant or anti-inflammatory (see, Suthanthiran et al., *Am. J. Kidney Disease,* 28:159–172 (1996)). Such nexuses are known in the art for several disease states, and more are expected to be discovered over time. Based on such nexuses, appropriate confirmatory in vitro and in vivo models of pharmacological activity, as well as toxicology, can be selected. The methods described herein can also be used to assess pharmacological selectivity and specificity, and toxicity.

Toxicology of Candidate Modulators

Once identified, candidate modulators can be evaluated for toxicological effects using known methods (see, Lu, *Basic Toxicology, Fundamentals, Target Organs, and Risk Assessment,* Hemisphere Publishing Corp., Washington (1985); U.S. Pat. No. 5,196,313 to Culbreth (issued Mar. 23, 1993) and U.S. Pat. No. 5,567,952 to Benet (issued Oct. 22, 1996). For example, toxicology of a candidate modulator can be established by determining in vitro toxicity towards a cell line, such as a mammalian i.e. human, cell line. Candidate modulators can be treated with, for example, tissue extracts, such as preparations of liver, such as microsomal preparations, to determine increased or decreased toxicological properties of the chemical after being metabolized by a whole organism. The results of these types of studies are often predictive of toxicological properties of chemicals in animals, such as mammals, including humans.

Alternatively, or in addition to these in vitro studies, the toxicological properties of a candidate modulator in an animal model, such as mice, rats, rabbits, or monkeys, can be determined using established methods (see, Lu, supra (1985); and Creasey, *Drug Disposition in Humans, The Basis of Clinical Pharmacology,* Oxford University Press, Oxford (1979)). Depending on the toxicity, target organ, tissue, locus, and presumptive mechanism of the candidate modulator, the skilled artisan would not be burdened to determine appropriate doses, $LD_{50}$ values, routes of administration, and regimes that would be appropriate to determine the toxicological properties of the candidate modulator. In addition to animal models, human clinical trials can be performed following established procedures, such as those set forth by the United States Food and Drug Administration (USFDA) or equivalents of other governments. These toxicity studies provide the basis for determining the efficacy of a candidate modulator in vivo.

Efficacy of Candidate Modulators

Efficacy of a candidate modulator can be established using several art recognized methods, such as in vitro methods, animal models, or human clinical trials (see, Creasey, supra (1979)). Recognized in vitro models exist for several diseases or conditions. For example, the ability of a chemical to extend the life-span of HIV-infected cells in vitro is recognized as an acceptable model to identify chemicals expected to be efficacious to treat HIV infection or AIDS (see, Daluge et al., *Antimicro. Agents Chemother.* 41:1082–1093 (1995)). Furthermore, the ability of cyclosporin A (CsA) to prevent proliferation of T-cells in vitro has been established as an acceptable model to identify chemicals expected to be efficacious as immunosuppressants (see, Suthanthiran et al., supra, (1996)). For nearly every class of therapeutic, disease, or condition, an acceptable in vitro or animal model is available. Such models exist, for example, for gastro-intestinal disorders, cancers, cardiology, neurobiology, and immunology. In addition, these in vitro methods can use tissue extracts, such as preparations of liver, such as microsomal preparations, to provide a reliable indication of the effects of metabolism on the candidate modulator. Similarly, acceptable animal models may be used to establish efficacy of chemicals to treat various diseases or conditions. For example, the rabbit knee is an accepted model for testing chemicals for efficacy in treating arthritis (see, Shaw and Lacy, *J. Bone Joint Surg.* (*Br*) 55:197–205 (1973)). Hydrocortisone, which is approved for use in humans to treat arthritis, is efficacious in this model which confirms the validity of this model (see, McDonough, *Phys. Ther.* 62:835–839 (1982)). When choosing an appropriate model to determine efficacy of a candidate modulator, the skilled artisan can be guided by the state of the art to choose an appropriate model, dose, and route of administration, regime, and endpoint and as such would not be unduly burdened In addition to animal models, human clinical trials can be used to determine the efficacy of a candidate modulator in humans. The USFDA, or equivalent governmental agencies, have established procedures for such studies.

Selectivity of Candidate Modulators

The in vitro and in vivo methods described above also establish the selectivity of a candidate modulator. It is recognized that chemicals can modulate a wide variety of biological processes or be selective. Panels of cells based on the present invention can be used to determine the specificity of the candidate modulator. Selectivity is evident, for example, in the field of chemotherapy, where the selectivity of a chemical to be toxic towards cancerous cells, but not towards non-cancerous cells, is obviously desirable. Selective modulators are preferable because they have fewer side effects in the clinical setting. The selectivity of a candidate modulator can be established in vitro by testing the toxicity and effect of a candidate modulator on a plurality of cell lines that exhibit a variety of cellular pathways and sensitivities. The data obtained from these in vitro toxicity studies can be extended animal model studies, including human clinical trials, to determine toxicity, efficacy, and selectivity of the candidate modulator.

Identified Compositions

The invention includes compositions such as novel chemicals, and therapeutics identified as having activity by the operation of methods, systems or components described herein. Novel chemicals, as used herein, do not include chemicals already publicly known in the art as of the filing date of this application. Typically, a chemical would be identified as having activity from using the invention and then its structure revealed from a proprietary database of chemical structures or determined using analytical techniques such as mass spectroscopy.

One embodiment of the invention is a chemical with useful activity, comprising a chemical identified by the method described above. Such compositions include small organic molecules, nucleic acids, peptides and other molecules readily synthesized by techniques available in the art and developed in the future. For example, the following combinatorial compounds are suitable for screening: peptoids (PCT Publication No. WO 91/19735, Dec. 26, 1991), encoded peptides (PCT Publication No. WO 93/20242, Oct. 14, 1993), random bio-oligomers (PCT Publication WO 92/00091, Jan. 9, 1992), benzodiazepines (U.S. Pat. No. 5,288,514), diversomeres such as hydantoins, benzodiazepines and dipeptides (Hobbs DeWitt, S. et al., Proc. Nat. Acad. Sci. USA 90: 6909–6913 (1993)), vinylogous polypeptides (Hagihara et al., J. Amer. Chem. Soc. 114: 6568 (1992)), nonpeptidal peptidomimetics with a Beta-D-Glucose scaffolding (Hirschmann, R. et al., J. Amer. Chem. Soc. 114: 9217–9218 (1992)), analogous organic syntheses of small compound libraries (Chen, C. et al., J. Amer. Chem. Soc. 116:2661 (1994)), oligocarbamates (Cho, C. Y. et al., Science 261: 1303 (1993)), and/or peptidyl phosphonates (Campbell, D. A. et al., J. Org. Chem. 59: 658 (1994)). See, generally, Gordon, E. M. et al., J. Med Chem. 37: 1385 (1994). The contents of all of the aforementioned publications are incorporated herein by reference.

The present invention also encompasses the identified compositions in a pharmaceutical compositions comprising a pharmaceutically acceptable carrier prepared for storage and subsequent administration, which have a pharmaceutically effective amount of the products disclosed above in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985). Preservatives, stabilizers, dyes and even flavoring agents may be provided in the pharmaceutical composition. For example, sodium benzoate, sorbic acid and esters of p-hydroxybenzoic acid may be added as preservatives. In addition, antioxidants and suspending agents may be used.

The compositions of the present invention may be formulated and used as tablets, capsules or elixirs for oral administration; suppositories for rectal administration; sterile solutions, suspensions for injectable administration; and the like. Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes), may be utilized.

The pharmaceutically effective amount of the composition required as a dose will depend on the route of administration, the type of animal being treated, and the physical characteristics of the specific animal under consideration. The dose can be tailored to achieve a desired effect, but will depend on such factors as weight, diet, concurrent medication and other factors which those skilled in the medical arts will recognize.

In practicing the methods of the invention, the products or compositions can be used alone or in combination with one another, or in combination with other therapeutic or diagnostic agents. These products can be utilized in vivo, ordinarily in a mammal, preferably in a human, or in vitro. In employing them in vivo, the products or compositions can be administered to the mammal in a variety of ways, including parenterally, intravenously, subcutaneously, intramuscularly, colonically, rectally, nasally or intraperitoneally, employing a variety of dosage forms. Such methods may also be applied to testing chemical activity in vivo.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage for the products of the present invention can range broadly depending upon the desired affects and the therapeutic indication. Typically, dosages may be between about 10 kg/kg and 100 mg/kg body weight, preferably between about 100 $\mu$g/kg and 10 mg/kg body weight. Administration is preferably oral on a daily basis.

The exact formulation, route of administration and dosage can be chosen by the individual physician in view of the patient's condition. (See e.g., Fingl et al., in The Pharmacological Basis of Therapeutics, 1975). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in Remington's Pharmaceutical Sciences, 18th Ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

For injection, the agents of the invention may be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art. Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g. by means of conventional mixing, dissolving, granulating, dragee-making, levitating, emulsifying, encapsulating, entrapping, or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dye-stuffs or pigments may be added to the tablets or dragee coatings for identification or to characterize different combinations of active compound doses.

EXAMPLES

Example 1

Fluorescence Properties of Cycloolefins Compared to Glass and Other Polymeric Materials To investigate the fluorescence properties of various selected materials, different polymeric films were tested for fluorescence emission at predetermined excitation wavelengths and compared to two types of glass sheets (standard). These experiments were conducted using a SPEX Fluorolog 111 Fluorimeter with excitation wavelengths between 315 and 425 nm. The films and glass materials were disposed on a holder. The sample was positioned with the excitation beam perpendicular to the sample face. The fluorescence emission from the sample was collected off angle at about 12.5 degrees. The material's fluorescence emission was reflected off of a mirror and onto a monochrometer. The emission radiation was selected by the monochromatic grating and was detected by the photomultiplier tube of the instrument. The SPEX Fluorolog 111 Fluorimeter utilizes Raman radiation lines of water to calibrate and background correct the instrument measurements from day to day. This background correction was performed each day before instrument use for calibration. The calibration file is stored with the measurements made that day and then subsequent measurements with the SPEX instrument can be compared directly and corrected for instrument fluctuation.

The materials tested were 1) glass sheets (Corning Glass Works cover-slip No 1 (catalog number 2935/583331) (average thickness between about 130 and 170 micrometers), 2) polystyrene films (ps1, ps2 (from Plastic Suppliers) and ps3 (from Dow Chemical Company), 3) polycarbonate films (pc1 (from General Electric Corporation) and pc2 (from Plastic Suppliers); 4) non-aromatic, alkyl polymers (nap; obtained from Mobil Oil Company), 5) cycloolefin copolymer film (coc; obtained from Hoechst, Topas (2 mil, or 50 micrometers thick)) and 6) Aclar (a fluorocarbon material from Allied Signal).

Table 2 shows the fluorescence normalized emission data over 400 to 650 nm at three different excitation wavelengths.

The data is normalized to glass and to correct for instrumentation fluctuation. Polystyrene, which is often used as a component of multi-well plates (see Table 1), generated high background fluorescence levels, consistent with its aromatic structure. Surprisingly, polycarbonate, which is often a biocompatible polymer, was generally better than polystyrene, especially at longer wavelengths. Surprisingly, the non-aromatic, alkyl polymer was generally the second best polymer across the range of wavelengths tested. Also surprisingly, the cycloolefin copolymer produced the best results and nearly approached the extremely low fluorescence levels of glass.

microscope. Background in the absence of a film was recorded and subtracted from signals in the presence of a film.

The materials tested were 1) glass sheets (Fisher coverslip Number 1 (Fisher Catalog number 12-542B (1996)), 2) polystyrene films (ps1, ps2 (from Plastic Suppliers) and ps3 (from Dow Chemical Company), 3) polycarbonate films (pc1 (from General Electric Corporation) and pc2 (from Plastic Suppliers); 4) non-aromatic, alkyl polymers (obtained from Mobil), 5) cycloolefin copolymer film (coc; obtained from Hoechst, Topas), and 6) Aclar (a fluorocarbon material from Allied Signal) and 7) Syran Wrap.

TABLE 2

| Material | Em = 400 | Em = 425 | Em = 450 | Em = 475 | Em = 500 | Em = 550 | Em = 600 | Em = 650 |
|---|---|---|---|---|---|---|---|---|
| Ex = 315 | | | | | | | | |
| Glass | 0.22513 | 0.25824 | 0.26817 | 0.30459 | 0.33107 | 0.38735 | 0.51316 | |
| Pc1 -5 mil | 3.31071 | 2.10230 | 2.01953 | 1.78778 | 1.41036 | 0.66876 | 0.60586 | |
| Pc2 -5 mil | 11.04128 | 7.04943 | 6.11517 | 5.18091 | 3.79367 | 1.70432 | 1.05317 | |
| Ps1 -2 mil | 2.45986 | 1.96447 | 1.93714 | 1.78340 | 1.52374 | 1.02494 | 1.18893 | |
| Ps2 - 2 mil | 2.20826 | 1.72697 | 1.69866 | 1.64204 | 1.48633 | 1.07582 | 1.18906 | |
| Ps3 - 2 mil | 4.55807 | 3.29823 | 3.00096 | 2.72352 | 2.34132 | 1.57409 | 1.98743 | |
| Nap - 1.5 mil | 1.01919 | 0.75307 | 0.62850 | 0.52942 | 0.50110 | 0.56622 | 1.12111 | |
| Nap - 1.5 mil | 0.52658 | 0.48978 | 0.42466 | 0.37654 | 0.38220 | 0.50960 | 1.00787 | |
| Coc - 2 mil | 0.40485 | 0.40485 | 0.34256 | 0.31142 | 0.31142 | 0.41617 | 0.83234 | |
| Aclar - .75 mil | 0.08473 | 0.08875 | 0.07864 | 0.07368 | 0.07503 | 0.09701 | 0.22497 | |
| Aclar - 3 mil | 0.27245 | 0.28586 | 0.26367 | 0.26522 | 0.29309 | 0.44479 | 1.03199 | |
| Ex = 350 | | | | | | | | |
| Glass | 0.30790 | 0.20526 | 0.23837 | 0.17547 | 0.16222 | 0.17878 | 0.25492 | |
| Pc1 - 5 mil | 0.77802 | 0.62572 | 0.60586 | 0.50323 | 0.42708 | 0.31452 | 0.33769 | |
| Pc2 - 5 mil | 3.96354 | 2.74616 | 2.20826 | 1.61373 | 1.24568 | 0.75024 | 0.62284 | |
| Ps1 - 2 mil | 1.28801 | 1.44858 | 2.22754 | 2.06013 | 1.78340 | 1.06594 | 0.84387 | |
| Ps2 - 2 mil | 1.01919 | 1.34477 | 1.85437 | 1.84021 | 1.64204 | 1.089g7 | 0.89180 | |
| Ps3 - 2 mil | 2.13182 | 2.68388 | 3.47092 | 3.14252 | 2.68388 | 1.57692 | 1.29381 | |
| Nap - 1.5 mil | 0.95408 | 0.80120 | 0.81536 | 0.59170 | 0.53508 | 0.58321 | 0.79554 | |
| Nap - 1.5 mil | 0.53791 | 0.48695 | 0.55206 | 0.39918 | 0.39918 | 0.48129 | 0.69079 | |
| Coc - 2 mil | 0.42466 | 0.38220 | 0.43033 | 0.31142 | 0.31142 | 0.38503 | 0.56056 | |
| Aclar - .75 mil | 0.08689 | 0.08710 | 0.08689 | 0.07327 | 0.07224 | 0.08050 | 0.10733 | |
| Aclar - 3 mil | 0.24045 | 0.23323 | 0.24974 | 0.21981 | 0.23375 | 0.31373 | 0.43756 | |
| Ex = 400 | | | | | | | | |
| Glass | | | 0.29134 | 0.21520 | 0.25492 | 0.18540 | 0.26817 | 0.43039 |
| Pc1 - 5 mil | | | 0.38073 | 0.30459 | 0.32114 | 0.22844 | 0.31783 | 0.48667 |
| Pc2 - 5 mil | | | 0.65115 | 0.59736 | 0.62284 | 0.43033 | 0.53791 | 0.77855 |
| Ps1 - 2 mil | | | 0.55347 | 0.55347 | 0.67646 | 0.43731 | 0.61155 | 0.91561 |
| Ps2 - 2 mil | | | 0.49544 | 0.50960 | 0.60869 | 0.46996 | 0.65115 | 1.00221 |
| Ps3 - 2 mil | | | 0.75873 | 0.80120 | 0.97107 | 0.63417 | 0.86065 | 1.24568 |
| Nap - 1.5 mil | | | 0.57754 | 0.59170 | 0.67663 | 0.50110 | 0.72476 | 1.08431 |
| Nap - 1.5 mil | | | 0.41900 | 0.39635 | 0.50394 | 0.42466 | 0.66248 | 1.05883 |
| Coc - 2 mil | | | 0.32558 | 0.33407 | 0.41900 | 0.37087 | 0.55489 | 0.87198 |
| Aclar - .75 mil | | | 0.06295 | 0.06295 | 0.07121 | 0.06966 | 0.10010 | 0.15686 |
| Aclar - 3 mil | | | 0.14138 | 0.14654 | 0.17750 | 0.20433 | 0.32405 | 0.47988 |

Example 2

Fluorescence Properties of Cycloolefins Compared to Glass and Other Polymeric Materials To further investigate fluorescence properties of various selected materials, different polymeric films were tested for fluorescence emission at predetermined excitation wavelengths and compared to two types off used silica glass sheets (standard). These experiments were conducted to simulate biochemical or cell-based assays that involve aqueous media. Therefore, films were mounted on a horizontal plastic holder to permit addition of a drop of aqueous media. Three milliliters of water were dispensed onto the film and fluorescence recorded using a Zeiss inverted fluorescence Table 3 shows the fluorescence normalized emission data at 460 nm at 350 and 405 nm (excitation wavelengths). The data is normalized to glass. Polystyrene, which is often used as a component of multi-well plates (see Table 1), generated high background fluorescence levels, consistent with its aromatic structure as in Example 1. In contrast to Example 1, polycarbonate, which is often a biocompatible polymer, was worse than polystyrene, especially at longer wavelengths. Generally consistent with Example 1, the non-aromatic, alkyl polymer was generally better than polystyrene across the range of wavelengths tested. Generally consistent with Example 1, the cycloolefin copolymer produced the best results and surprisingly out preformed the extremely low fluorescence levels of glass. Aclar film also surprisingly produced either low or extremely low fluorescence values relative to glass. However, Aclar films were later found to have undesirable manufacturing characteristics, such as bonding to other materials and suitability for use in injection molding.

TABLE 3

| Material | 350ex/460em | Rank | Material | 405ex/460em | rank |
|---|---|---|---|---|---|
| Fisher #1 coverslip | 1.02 | 1 | Fisher #1 coverslip | 1.03 | 1 |
| Polycarbonate 5 mil | 6.91 | 6 | Polycarbonate 5 mil | 19.79 | 6 |
| Polystyrene 2 mil | 3.57 | 5 | Polystyrene 2 mil | 3.36 | 4 |
| NAP 1.5 ml | 2.06 | 3 | NAP 1.5 ml | 5.76 | 3 |
| NAP 1.5 ml | 1.33 | 3 | NAP 1.5 ml | 3.51 | 3 |
| coc#2 2 mil | 1.58 | 2 | coc#2 2 mil | 2.60 | 2 |
| coc#1 2 mil | 1.22 | 2 | coc#1 2 mil | 1.59 | 2 |
| aclar sample (>2 yrs old) | 2.62 | 4 | Aclar sample (>2 yrs old) | 9.08 | 5 |

| Material | 350ex/460em | Rank | Material | 405ex/460em | rank |
|---|---|---|---|---|---|
| Fisher #1 coverslip | 1.00 | 5 | Fisher #1 coverslip | 1.00 | 1 |
| Polycarbonate 5 mil | 5.15 | 9 | Polycarbonate 5 mil | 17.75 | 8 |
| polystyrene 1 mil | 2.01 | 7 | Polystyrene 1 mil | 2.53 | 7 |
| coc#2 A 2 mil | 1.09 | 6 | Coc#2 A 2 mil | 1.71 | 4 |
| coc#2 B 2 mil | 0.89 | 4 | Coc#2 B 2 mil | 1.65 | 3 |
| coc#1 2 mil | 0.86 | 3 | coc#1 2 mil | 1.47 | 2 |
| Aclar 3 mil (<1 yr old) | 0.71 | 1 | aclar 3 mil (<1 yr old) | 2.34 | 6 |
| aclar 0.75 mil (<1 yr old) | 0.64 | 1 | aclar 0.75 mil (<1 yr old) | 2.14 | 5 |
| syran wrap | 4.18 | 8 | syran wrap | 22.12 | 9 |

Example 3

Cycloolefins are Not CytoToxic To Cultured Cells

The cytotoxicity of cycloolefin was evaluated by incubating cells in cycloolefin multi-well plates for 60 hours at 37° C. 1.8 µL volumes of media containing about 90 Chinese hamster ovary (CHO) were placed in cycloolefin multi-well plates using a tapered pipette. A glass cover was placed over the wells to prevent evaporation. Cells were incubated for 60 hours in a 5% $CO_2$, 37° C., 90% RH incubator. Cells were then tested for viability by loading with the vital dye calcein. The CHO cells were loaded by incubation in a solution containing 4 µM calcein/AM for 30 minutes at room temperature. Cells were inspected using both phase contrast microscopy to determine the total number of cells and fluorescence microscopy to determine the number of live cells. Approximately, greater than 95% of cells were alive as indicated by loading with calcein dye (approximately 200 cells/well).

Example 4

Cycloolefins are Not CytoToxic To Cultured Cells and can be Used for Drug Screening Assays To investigate the cytotoxic properties of cyclolefins, cycloolefin film were tested using an assay for cell viability. CCF2 a vital dye, as described in PCT publication WO96/30540 (Tsien), diffuses into cells and is trapped by living cells having esterase activity that cleaves ester groups on the molecules which results in a negatively charged molecule that is trapped inside the cell. Trapped dye appears green inside of living cells and turns blue in the presence of beta-lactamase. CCF2 was incubated with Jurkat cells for at least hour in a 1 microliter well having black walls and a cycloolefin bottom, and fluorescence was appropriately monitored. These Jurkat cells were constitutively expressing β-lactamase. Cells were cultured for 60 hours in the conditions of Example 3. After 60 hours, β-lactamase activity was measured using CCF2. Cells appeared blue indicating that β-lactamase was indeed active in these cells, which normally do not contain β-lactamase. These results demonstrate that cycloolefins can be used with sensitive fluorescent assays because the films yield low fluorescent backgrounds. This is particularly beneficial because it permits smaller assay volumes (e.g. 2 microliters or less) and the measurement of smaller signals (e.g., from fewer cells or fewer number of isolated biochemical targets).

Example 5

High Density Multi-Well Platforms

FIG. 2 shows a preferred multi-well platform of the present invention. A 240 well (5×48 wells) injection molded multi-well platform and a 45 well (three sets of 3×5 wells) multi-well platform, each having a well-center-to-well-center distance of 1.5 mm, were made.

Injection molded multi-well platform

This multi-well platform comprised a frame, wherein the wall of a well was disposed in the frame. The frame was made of cycloolefin copolymer, which was made optically opaque with about 2% black pigment (OmniColor® IM0055. Reed Spectrum, Holden, Mass.). The frame was about 3.25 mm thick and was made by injection molding. The bottom of the frame was substantially flat.

Each well had a bottom, which had a high transmittance portion. The bottom had a thickness of about 50 micrometers and was made of clear, flat, cycloolefin copolymer film. The frame and bottom were joined by heat-sealing to from the wells. The wall of each well was chamfered at about 2.87 degrees and the well-center-to-well-center distance was about 1.5 millimeters. The diameter of the wells at the bottom of the frame was about 0.95 mm.

The multi-well platform further comprised a groove 21 that surrounded three of the four sides of the well matrix 22. These multi-well platforms were used in fluorescent based assays as described in the following examples.

Machined multi-well platform

Alternatively, the frame was machined from an acrylic plate (black Acrylic butyl styrene (black ABS)) made optically opaque with about 2% to 4% of back pigment, and a bottom. The bottom was a glass plate 0.01 mm thick (borosilicate glass, Precision Glass) attached to the bottom of the frame by adhesive silicone. The frame and the bottom were combined for form a multi-well platform 3.13 mm thick. In this multi-well platform the wells were not chamfered and the well-center-to-well center distance was about 1.5 millimeters. The diameter of each well was about 0.95 mm.

Example 6

Detection of Protease Activity in a Machined Multi-Well Platform

In this example, trypsin activity in the machined multi-well platform described in Example 5 was detected using a green fluorescent protein tandem construct comprising two green fluorescent protein molecules coupled by a linker as reported by Tsien et al. (WO 97/28261). The two green-fluorescent protein molecules can exhibit fluorescence resonance energy transfer between themselves, and the linker comprises a trypsin substrate. When a sample comprises this intact construct, fluorescence resonance energy transfer between the green fluorescent protein molecules causes the sample to fluoresce at 535 nm when excited with light of about 400 nm. When the linker is cleaved with a protease such as trypsin, the green fluorescent protein molecules no longer exhibit fluorescence resonance energy transfer, and the sample will fluoresce at 460 nm when exited with light of about 400 nm. The increase in the ratio of the emission of 460 nm and 535 nm correlates with the protease activity in the sample.

To individual wells, 2.0 µL of the same 1 µM solution of the tandem construct with or without 0.015 nM trypsin were added. The bottom of each well was excited with light of 400 nm, and the emission at 460 nm and 535 nm measured through the bottom of each well. The samples were incubated at room temperature for thirty minutes. The bottom of each well was exited again with light of 400 nm, and the emission at 460 nm and 535 nm measured through the bottom of each well. As shown in Table 4, addition of trypsin to the wells consistently elicited a greater than four fold increase in the emission ratio.

TABLE 4

| Well Number | 460/535 Emission Ratio | |
|---|---|---|
| | No Trypsin | Trypsin Added |
| 1 | 0.20 | 1.00 |
| 2 | 0.20 | 0.94 |
| 3 | 0.20 | 0.94 |
| 4 | 0.20 | 0.98 |
| 5 | 0.20 | 0.93 |

Example 7

Detection of an Activated Reporter Gene in a Cell

In this example, a concentration response of carbachol in a Jurkat cell line stably transfected with a plasmid encoding the M1 muscarinic receptor and a NF-AT-β-lactamase reporter gene. In this transfected cell line, carbachol acts to stimulate the M1 muscarinic receptor so that the NFAT-β-lactamase reporter gene is expressed. When expressed, this gene produces β-lactamase, which can then be detected using a fluorescent probe, such as CCF2/AM, that exhibits different emissions when intact and cleaved by β-lactamase as reported by, for example, Tsien et al. (WO 96/30540).

Jurkat cells used in this example were made using the following procedures. Wild-type Jurkat cells were transfected with plasmid 3XNFAT-blax by electroporation (regarding the plasmid 3XNFAT-blax, see generally Fiering, *Genes and Development*, 4:1823–1834 (1990)). This plasmid is driven by the IL-2 minimum promoter. A portion of this population of transfected cells was seeded into 96-well plates with limited dilution and selected by Zeocin® (250 µg/ml). The clones in each well were screened for CCF2-AM staining in the presence and the absence of 10 nM PMA/2 µM ionomycin (Calbiochem). FACS sorting was used to isolate individual clones, which were further transfected with pcDNA3-M1, which comprises pcDNA3 (Invitrogen) configured such that nucleic acids encoding M1 can be expressed. These transfected cells were selected using G418 (1 mg/ml) for about 3 weeks. The clones in each well were screened for CCF2-AM staining in the presence and absence of 30 µM Carbachol (Calbiochem). FACS sorting was used to isolate individual clones.

Transfected Jurkat cells in 1.8 µL of RPMI buffer were dispensed at approximately 500 cells per well into individual wells of injection molded multi-well platform described in Example 5. These wells contained 0.3 to 31 nL of stock carbachol solution. Cells were incubated for three hours at 37° C. The solution in each well was made one µM CCF2/AM. The bottom of each well was excited with light of 400 nm and the emission of light at 460 nm and 535 nm was detected and measured through the bottom of the well. The ratio of the emission at these wavelengths is correlated with β-lactamase activity in the cell, which is correlated with the stimulation of the cell. As shown in Table 5, the stimulation of the cells, as measured by the ratio of emission at 460 nm and 535 nm, was dependent upon the concentration of carbachol provided in the well.

TABLE 5

| Carbachol Concentration (µM) | Emission Ratio (460/535) |
|---|---|
| 0.09 | 1.28 |
| 0.17 | 2.44 |
| 0.43 | 3.38 |
| 0.87 | 5.90 |
| 1.70 | 7.70 |
| 4.30 | 8.90 |

Example 8

Detection of an Activated Reporter

In this example, a Jurkat cell line stably transfected with a CMV-β-lactamase reporter gene. When expressed, this gene produces β-lactamase, which can then be detected using a fluorescent probe, CCF2/AM, that exhibits different fluorescent emissions when intact or cleaved by β-lactamase as reported by Tsien et al. (WO 96/30540). The same Jurkat cell line without the CMV-β-lactamase reporter gene was used as a control.

The Jurkat cells used in this example were obtained in a similar way as described in the Example above. Briefly, pcDNA3-bla, which encodes β-lactamase operatively linked to the CMV promoter, was transfected into wild type Jurkat cells. The G418 (1 mg/ml) selected population were stained with CCF2-AM and FACS sorted.

Control and transfected Jurkat cells in RPMI buffer were dispensed at approximately 800 cells per well into individual wells of the machined multi-well platform described in Example 5. Cells were incubated for ninety minutes at 23° C. in an RPMI buffer containing 10 μM CCF2/AM as described above. The bottom of each well was excited with light of 400 nm and the emission of light at 460 and 535 nm was detected and measured through the bottom of the well. The emission at that wavelength is correlated with β-lactamase activity in the cell, which is correlated with the expression of β-lactamase in the cell. As shown in Table 6, about 800 cells expressing β-lactamase showed at least a twelve-fold increase in the ration of emission at 460 and 535 compared to control cells.

TABLE 6

| Well Number | Cell Type | Emission Ratio 460/535 |
|---|---|---|
| 1 | Wild Type | 1 |
| 2 | Wild Type | 1 |
| 3 | Wild Type | 1 |
| 4 | Wild Type | 1 |
| 5 | Wild type | 1 |
| 6 | CMV- β-lactamase | 13 |
| 7 | CMV- β-lactamase | 13 |
| 8 | CMV- β-lactamase | 13 |
| 9 | CMV- β-lactamase | 13 |
| 10 | CMV- β-lactamase | 13 |

Publications

All publications, including patent documents and scientific articles, referred to in this application are incorporated by reference in their entirety for all purposes to the same extent as if each individual publication were individually incorporated by reference.

All headings are for the convenience of the reader and should not be used to limit the meaning of the text that follows the heading, unless so specified.

What is claimed is:

1. A multi-well platform, comprising:
   a) a plurality of wells, each well comprising:
      i) a wall having less fluorescence than a polystyrene-wall of 90 percent of said wall's thickness; and
      ii) a bottom.
2. The multi-well platform of claim 1 wherein said bottom has a high transmittance and a thickness less than about 450 microns.
3. The multi-well platform of claim 2 wherein said bottom has less fluorescence than a polystyrene-bottom of 90 percent of said bottom's thickness.
4. The multi-well platform of claim 3 wherein said bottom produces about 200 percent or less of the fluorescence compared to fused silica glass of 100 microns thickness throughout the following wavelength ranges: excitation wavelengths between about 300 to 400 nm and at emission wavelengths between about 300 to 800 nm.
5. The multi-well platform of claim 1 further comprising a frame and wherein said wells are disposed in said frame.
6. The multi-well platform of claim 1 wherein said bottom has less fluorescence than a polystyrene-bottom of 90 percent of said bottom's thickness.
7. The multi-well platform of claim of claim 1 wherein said plurality of wells comprises 864 or more wells.
8. The multi-well platform of claim of claim 1 wherein said plurality of wells comprises between 96 and 864 wells.
9. The multi-well platform of claim 1 wherein said wall of each of said wells is formed of an opaque material.
10. The multi-well platform of claim 1 wherein said wall of each of said wells is coated with an optically opaque material.
11. The multi-well platform of claim 1 wherein said wall of each of said wells is formed of a cycloolefin material.
12. The multi-well platform of claim 1 wherein said bottom is made of polystyrene.
13. The multi-well platform of claim 1 wherein said wells have a depth of between 3 millimeters and 20 mm.
14. A multi-well platform, comprising:
    a) a plurality of wells, each well comprising:
       i) a wall formed of a material which emits 200 percent or less of the fluorescence compared to fused silica glass of 100 microns thickness throughout the following wavelength ranges: excitation wavelengths between about 300 to 400 nm and at emission wavelengths between about 300 to 500 nm, and
       ii) a bottom.
15. The multi-well platform of claim 14 wherein said bottom has a high transmittance and a thickness less than about 450 microns.
16. The multi-well platform of claim 15 wherein said bottom has less fluorescence than a polystyrene-bottom of 90 percent of said bottom's thickness.
17. The multi-well platform of claim 14 wherein said bottom has less fluorescence than a polystyrene-bottom of 90 percent of said bottom's thickness.
18. The multi-well platform of claim 14 further comprising a frame and wherein said wells are disposed in said frame.
19. The multi-well platform of claim 16 wherein said bottom produces about 200 percent or less of the fluorescence compared to fused silica glass of 100 microns thickness throughout the following wavelength ranges: excitation wavelengths between about 300 to 400 nm and at emission wavelengths between about 300 to 800 nm.
20. The multi-well platform of claim of claim 14 wherein said plurality of wells comprises 864 or more wells.
21. The multi-well platform of claim of claim 14 wherein said plurality of wells comprises between 96 and 864 wells.
22. The multi-well platform of claim 14 wherein said wall of each of said wells is formed of an opaque material.
23. The multi-well platform of claim 14 wherein said wall of each of said wells is coated with an optically opaque material.
24. The multi-well platform of claim 14 wherein said wall of each of said wells is formed of a cycloolefin material.
25. The multi-well platform of claim 14 wherein said bottom is made of polystyrene.
26. The multi-well platform of claim 14 wherein said wells have a depth of between 3 millimeters and 20 mm.
27. The multi-well platform of claim 14 wherein said wells have a volume of 10 microliters or less.
28. The multi-well platform of claim 14 wherein said plurality of wells is formed by injection molding process.

* * * * *